United States Patent [19]
Faraci et al.

[11] Patent Number: 5,889,010
[45] Date of Patent: Mar. 30, 1999

[54] BENZIMIDAZOLE DERIVATIVES HAVING DOPAMINERGIC ACTIVITY

[75] Inventors: William S. Faraci, East Lyme; Anton F. J. Fliri, Norwich; Brian T. O'Neill; Mark A. Sanner, both of Old Saybrook; Stevin H. Zorn, North Stonington, all of Conn.

[73] Assignee: Pfizer Inc., New York, N.Y.

[21] Appl. No.: 793,032

[22] PCT Filed: May 18, 1995

[86] PCT No.: PCT/IB95/00378

§ 371 Date: Jan. 31, 1997

§ 102(e) Date: Jan. 31, 1997

[87] PCT Pub. No.: WO96/04250

PCT Pub. Date: Feb. 15, 1996

[51] Int. Cl.⁶ .......................... A01N 43/60; C07D 403/00
[52] U.S. Cl. ............................ 514/255; 544/370
[58] Field of Search ............... 514/255; 544/370

[56] References Cited

U.S. PATENT DOCUMENTS

| | | | |
|---|---|---|---|
| 3,472,854 | 10/1969 | Archer | 260/268 |
| 3,573,310 | 3/1971 | Van Dyke, Jr. | 260/268 |
| 3,634,441 | 1/1972 | Welstead, Jr. et al. | 260/296 |
| 3,635,982 | 1/1972 | Potoski et al. | 260/268 |
| 3,644,414 | 2/1972 | Helsley | 260/326.3 |
| 3,647,790 | 3/1972 | Potoski et al. | 260/244 |
| 3,794,651 | 2/1974 | Helsley et al. | 260/268 |
| 4,002,623 | 1/1977 | Kadin | 260/247.2 |
| 4,200,641 | 4/1980 | Vandenberk et al. | 424/267 |
| 4,707,487 | 11/1987 | Arrang et al. | 514/326 |
| 4,954,503 | 9/1990 | Strupczewski et al. | 514/254 |

FOREIGN PATENT DOCUMENTS

| | | |
|---|---|---|
| 904945 | 12/1986 | Belgium . |
| 0010398 | 4/1980 | European Pat. Off. . |
| 0197840 | 10/1986 | European Pat. Off. . |
| 200322 | 11/1986 | European Pat. Off. . |
| 0409692 | 1/1991 | European Pat. Off. . |
| 0511074 | 10/1992 | European Pat. Off. . |
| 0522915 | 1/1993 | European Pat. Off. . |
| 0526434 | 2/1993 | European Pat. Off. . |
| 0548813 | 6/1993 | European Pat. Off. . |
| 0571243 | 11/1993 | European Pat. Off. . |
| 2017265 | 10/1970 | Germany . |
| 2714437 | 10/1977 | Germany . |
| 9503298 | 2/1995 | WIPO . |
| 9507863 | 3/1995 | WIPO . |

OTHER PUBLICATIONS

Estep et. al., "Synthesis & Structure–Activity Relationship . . . ", J. Med. Chem., vol. 38(14), pp. 2582–2595, Jul. 7, 1995.

Stephens, J. A., et al., "The Synthesis of Some Substituted Naphth[1,2]imidazole Derivatives", J. Amer. Chem. Soc., 73, pp. 4297–4299 (1951).

Rogers, G. T., et al., "Synthesis of 3–Methylisoguanine [6–Amino–3–methylpurin–2(3H)–one]", J. Chem. Soc. (C), pp. 2364–2366 (1971).

King, F. E., et al., "The Synthesis of Benziminazoles from ortho–Phenylenediamines and Imino–ethers", J. Chem. Soc., pp. 1396–1400 (1949).

Haley, C. A. C., et al., "Organic Reactions in Aqueous Solution at Room Temperature. Part I. The Influence of pH on Condensations involving the Linking of Carbon to Nitrogen and of Carbon to Carbon", J. Chem. Soc., 39, pp. 3155–3174 (1951).

Tserng, Kou–Yi, et al., "Novel Lossen Rearrangements of 3–Benzenesulfonyloxy(1H–and 1–methyl)–2,4–quinazolinediones induced by Alkoxide Ions", J. Org. Chem., 38, pp. 3498–3502 (1973).

Sunahara, R. K., et al., "Human dopamine $D_1$ receptor encoded by an intronless gene on chromosome 5", Nature, vol. 347, pp. 80–83 (1990).

Van Tol. et al., "Cloning of the gene for a human dopamine $D_4$ receptor with high affinity for the antipsychotic clozapine", Nature, vol. 350, pp. 610–614 (London, 1991); and.

(List continued on next page.)

Primary Examiner—Mukund J. Shah
Assistant Examiner—Tamthom T. Ngo
Attorney, Agent, or Firm—Peter C. Richardson; Paul H. Ginsburg; Raymond M. Speer

[57] ABSTRACT

Pharmaceutically active benzimidazole derivatives are disclosed comprising compounds of the formula:

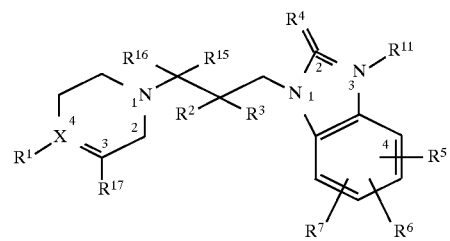

particularly wherein X is nitrogen, $R^1$ is phenyl or heteroaryl, and one of $R^2$ or $R^3$ is hydroxy. Said compounds have D4 dopaminergic receptor binding activity and consequently are useful as active ingredients in pharmaceutical compositions and methods of treatment for sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, ocular disorders, congestive heart failure, chemical dependencies, vascular and cardiovascular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal.

10 Claims, No Drawings

OTHER PUBLICATIONS

Mathias, L. J., et al., "Synthesis of Formamidines and Benzimidazoles", Synth. Commun., 5(6), pp. 461–469 (1975).

K. Freter, V. Fuchs, E. Barsumian, and J. T. Oliver, Arzneim.–Forsch./Drug Res., "4–(Indolyl–3–)–1–(Benzimidazolonylalkyl)–Piperidines, A Novel Group of Potential Anti-allergy Compounds", 35(1), nR. LA (1985).

Josef Sawlewicz, and Marian Grzybowski, Acta Pol. Pharm., "Benzimidazole Derivatives. IX. Synthesis of Amino Alcoholes and Thioethers Derived From 1–(2–Hydroxy–3–Chloropropyl)–2–Alkylbenzimidazoles", (Unable to Obtain Copy of complete Document: See Attached Chemical Abstract of Document).

1

BENZIMIDAZOLE DERIVATIVES HAVING DOPAMINERGIC ACTIVITY

This is a 371 application of PCT/IB95/00378, filed on May 18, 1995.

The present invention relates to novel pharmacologically active benzimidazole derivatives and their acid addition salts. The compounds of this invention exhibit central dopaminergic activity and are useful in the treatment of central nervous system (CNS) disorders. They act preferentially on the D4 dopamine receptor.

It is generally accepted knowledge that dopamine receptors are important for many functions in the animal body. For example, altered functions of these receptors participate in the genesis of psychosis, addiction, sleep, feeding, learning, memory, sexual behavior, regulation of immunological responses and blood pressure. Since dopamine receptors control a great number of pharmacological events and, on the other hand, not all of these events are presently known, there is a possibility that compounds that act preferentially on the D4 dopamine receptor may exert a wide range of therapeutic effects in humans.

European Patent Application EP 0526434, which was published on Feb. 3, 1993, referred to a class of substituted benzimidazol-2-ones that contain 1-(aryl and heteroaryl)4-propyl-piperidine substituents and states that such compounds were found to be centrally acting serotinergic agents. European Patent Application EP 0548813, which was published on Jun. 30, 1993, refers to a class of substituted indole derivatives that contain 1-[3-(4-aryl and heteroaryl) piperazine-1-yl]propyl substituents and states that such compounds were found to be centrally acting serotinergic agents. German Patent Application DE 2017265, which was published on Oct. 15, 1970, refers to a class of substituted 1-[3-(4-phenyl)piperazin-1-yl]propyl-2-methyl-1H-benzimidazoles and states that such compounds were tested in mice and found to have bronchodilating effects. U.S. Pat. No. 4,200,641, which was issued on Apr. 29, 1980, and German Patent DE 2714437, which was published on May 11, 1989, refer to a series of 1-[3-(4-benzhydryl)piperazin-1-yl]propyl-2,3-dihydro-1H-benzimidazol-2-ones. These compounds were tested in mice and found to have antihistaminic activity. U.S. Pat. No. 4,954,503, which issued on Dec. 31, 1991, refers to a series of indazole derivatives that contain 1-(aryl and heteroaryl) 4propyl-piperidine substituents and states that such compounds were found to exhibit antipsychotic and analgesic activity in mice.

The benzimidazole and benzimidazolone moiety has been used as a generic substituent in the preparation of a variety of structurally different classes of compounds that exhibit activity on the CNS systems. Examples can be found in Belgium Patent Application BE 904,945, which was published on Dec. 18, 1986, U.S. Pat. No. 4,954,503, which issued on Dec. 31, 1991, and European Patent Application EP 200,322, which was published on Feb. 28, 1990.

The present inventors have synthesized several substituted 1-[4-(aryl or heteroaryl)-piperazin-1-yl]-3-(2-propyl-benzoimidazol-1-yl)-propan-2-ol; 1-{3-[4-(aryl or heteroaryl)-piperazin-1-yl]-2-hydroxy-propyl}-1,3-dihydro-benzoimidazol-2-one and 1-{3-[4-(aryl or heteroaryl)-piperazin-1-yl]-propyl}-1H-benzoimidazole derivatives that posses central dopaminergic activity. These compounds have a preference for D4-dopamine receptor.

SUMMARY OF THE INVENTION

This invention relates to compounds of the formula

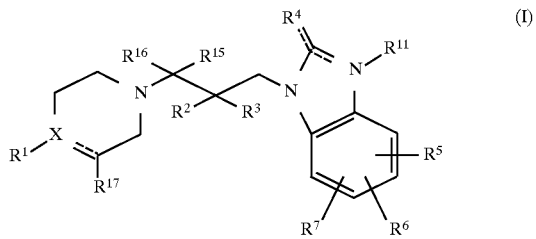

wherein each of the dotted lines represents an optional double bond;

X is carbon or nitrogen;

$R^1$ ($C_1$–$C_4$)alkyl is benzyl, aryl selected from phenyl, indanyl and naphthyl, or heteroaryl selected from pyridyl, thienyl, furyl, thiazolyl, isothiazolyl, oxazolyl, isoxazolyl, triazolyl, quinolyl and imidazolyl, wherein each of the foregoing aryl, heteroaryl and ($C_1$–$C_4$)alkyl groups, and the phenyl moiety of the benzyl group, may optionally be substituted with one or more substituents, preferably with from zero to two substituents, independently selected from halo (e.g., chloro, fluoro, bromo or iodo), ($C_1$–$C_6$)alkyl optionally substituted with from one to three fluorine atoms, ($C_1$–$C_6$)alkoxy optionally substituted with from one to three fluorine atoms, cyano, —C(=O)$R^8$, aryl and heteroaryl, wherein said aryl is selected from phenyl, indanyl and naphthyl and said heteroaryl is selected from pyridyl, thienyl, furyl, thiazolyl, isothiazolyl, oxazolyl, isoxazolyl, triazolyl, quinolyl and imidazolyl;

or, when X is nitrogen, $R^1$ may optionally form, together with X, $R^{17}$ and the carbon atom to which $R^{17}$ is attached, a tetrohydroquinoline ring;

$R^2$ and $R^3$ are independently selected from hydrogen, hydroxy, ($C_1$–$C_6$)alkyl, ($C_1$–$C_6$) alkoxy, cyano, —CONH$_2$ and —NHC(=O)$R^9$, or $R^2$ and $R^3$ together form an oxo group;

$R^4$ is hydrogen, sulfur, oxygen, ($C_1$–$C_6$)alkyl, amino, —NHR$^{10}$, —SR$^{10}$, OR$^{10}$ or hydroxy;

$R^5$, $R^6$ and $R^7$ are independently selected from hydrogen, halo (e.g., chloro, fluoro, bromo or iodo), cyano, ($C_1$–$C_6$) alkyl optionally substituted with from one to three fluorine atoms, ($C_1$–$C_6$)alkoxy optionally substituted with from one to three fluorine atoms, ($C_1$–$C_6$)alkylsulfonyl, ($C_1$–$C_6$) acylamino, (phenyl)[($C_1$–$C_6$)acyl]amino, amino, ($C_1$–$C_6$) alkylamino, di-($C_1$–$C_6$)alkylamino, aryl and heteroaryl, wherein said aryl is selected from phenyl, naphthyl and indanyl, and said heteroaryl is selected from pyridyl, thienyl, furyl, thiazolyl, isothiazolyl, oxazolyl, isoxazolyl, triazolyl, quinolyl and imidazolyl;

$R^8$, $R^9$ and $R^{10}$ are independently selected from hydrogen and ($C_1$–$C_6$ )alkyl; and $R^{11}$ is hydrogen, ($C_1$–$C_6$)alkyl or benzyl, wherein the phenyl moiety of said benzyl may optionally be substituted with one or more substituents, preferably with from zero to two substituents, independently selected from halo (e.g., fluoro, chloro, bromo, or iodo), ($C_1$–$C_6$)alkyl optionally substituted with from one to three fluorine atoms, ($C_1$–$C_6$) alkoxy optionally substituted wit h fro m one to three fluorine atoms, amino, cyano, ($C_1$–$C_6$)alkylamino and di-($C_1$–$C_6$)alkylamino;

each of $R^{15}$ and $R^{16}$ is selected, independently, from hydrogen, methyl, cyano, —(C=O)—NH$_2$ and —CH$_2$—O—($C_1$–$C_6$)alkyl;

$R^{17}$ is hydrogen or, when X is nitrogen, $R^{17}$ may optionally form, together with the carbon to which it is attached, $R^1$ and X, a tetrahydroquinoline ring;

with the proviso that: (a) $R^4$ can not be either oxygen or hydroxy when all of $R^2$, $R^3$, $R^{15}$ and $R^{16}$ are hydrogen; (b) when the five membered ring of formula I contains a double bond, $R^{11}$ is absent; (c) when $R^4$ is sulfur or oxygen, $R^4$ is double bonded to the carbon to which is attached and such carbon is single bonded to both adjacent ring nitrogen atoms; and (d) when X is nitrogen and is double bonded to an adjacent carbon, $R^1$ is absent.

The compounds of formula I that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

This invention also relates to the pharmaceutically acceptable acid addition salts of compounds of the formula 1.

The term "one or more substituents", as used herein, includes from one to the maximum number of substituents possible based on the number of available bonding sites.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

Preferred compounds of this invention include the following:

5-Fluoro-1-{3-[(4-fluoro-phenyl)-piperazin-1-yl]butyl}-1,3-dihydro-benzoimidzol-2-one;
1-Benzoimidazol-1-yl-3-[4-(4-fluoro-phenyl)-piperazin-1-yl]-propan-2-ol;
1-(5-Chloro-benzoimidazol-1-yl)-3-[4-(4-fluoro-phenyl)-piperazin-1-yl]-propan-2-ol;
1-{3-[4-(4-Fluoro-phenyl)-piperazin-1-yl]-propyl}-5-trifluoromethyl-1H-benzolmidazole;
1-{3-[4-(4-Fluoro-phenyl)-piperazin-1-yl]-propyl}-1H-benzoimidazole;
1-{3-[4-(4-Fluoro-phenyl)-piperazin-1-yl]-propyl}-3-methyl-1,3-dihydrobenzoimidazol 2-one;
1-Benzoimidazol-1-yl-3-(4-o-tolyl-piperazine-1-yl)-propan-2-ol;
1-Benzoimidazol-1-yl-3-(4-m-tolyl-piperazine-1-yl)-propan-2-ol;
1-Benzoimidazol-1-yl-3-(4-p-tolyl-piperazin-1-yl)-propan-2-ol;
1-Benzoimidazol-1-yl-3-{4-chloro-phenyl)-phenyl-methyl]-piperazin-1 -yl]-propan-2ol; -1-Benzoimidazol-1-yl-3-[4-(2-chloro-phenyl)-piperazin-1-yl]-propan-2-ol;
1-Benzoimidazol-1-yl-3-[4-(4-chloro-phenyl)-piperazin-1-yl]-propan-2-ol;
1-Benzoimidazol-1-yl-3-[4-(3-chloro-phenyl)-piperazin-1-yl]-propan-2-ol;
1-Benzoimidazol-1-yl-3-[4-(3-chloro-phenyl)-piperazin-1-yl]-propan-2-ol;
1-Benzoimidazol-1-yl-3-(4-pyrimidin-2-yl-piperazin-1-yl)-propan-2-ol;
1-Benzoimidazol-1-yl-3-(4-naphthalen-1-yl-piperazin-1-yl)-propan-2-ol;
1-Benzoimidazol-1-yl-3-[4-(3-trifluoromethyl-phenyl)-piperazin-1-yl]-propan-2-ol;
1-Benzoimidazol-1-yl-3-(4-benzyl-piperazin-1-yl)-propan-2-ol;
1-Benzoimidazol-1-yl-3-[4-(2-trifluoromethyl-benzyl)-piperazin-1-yl]-propan-2-ol;
1-Benzoimidazol-1-yl-3-[4-(2-ethoxy-benzyl)-piperazin-1-yl]-propan-2-ol;
1-Benzolmidazo 1-yl-3-{4-{3-(3-trifluoromethyl-phenyl)-propyl-piperazin-1-yl}-propan-2-ol;
1-Benzoimidazol-1-yl-3-{4-[2-(3-trifluoromethyl-phenyl)-ethyl]-piperazin-1-yl}-propan-2-ol;
5-Fluoro-1-{3-[4-(4-fluoro-phenyl)-piperazin-1-yl]-propyl}-2-methyl-1H -benzoimidazole; and
5-Fluoro-1-{3-[4-(4-fluoro-phenyl)-3,6-dihydro-2H-pyridin-1-yl]-propyl}-2-1H-benzoimidazole.

Other compounds of this invention include the following:
(4-Chloro-2-nitro-phenyl)-{3-[4-(4-fluoro-phenyl)-piperazin-1-yl]-propyl}-amine;
{3[4-(4-Fluoro-phenyl)-piperazin-1-yl]-propyl}-(2-nitro4-trifluoromethyl-phenyl)-amine;
4-Chloro-N1-{3-[4-(4-fluoro-phenyl)-piperazin-1-yl}-propyl}-benzene-1,2-diamine;
1-(4,5-Dichloro-2-nitro-phenylamino)-3-[4-(4fluoro-phenyl)-piperazin-1-yl]-propan-2-ol;
1-[4-(4-Fluoro-phenyl)-piperazin-1-yl]-3-(2-phenyl-benzoimidazol-1-yl)-propan-2-ol;
1-[4-(4-Fluoro-phenyl)-piperazin-1-yl](2-propyl-benzoimidazol-1-yl)-propan-2-ol;
1-[4-(4-Fluoro-phenyl)-piperazin-1-yl]-3-(2-methyl-benzoimidazol-1 -yl)-propan-2-ol;
5-Fluoro-1-(3-[4-(4-fluoro-phenyl)-piperazin-1-yl]-propyl)-2-methyl-1H-benzoimidazole;
5Chloro-1-(3-[4-(4-fluoro-phenyl)-piperazin-1-yl]-2-hydroxy-propyl)-1,3-dihydro -benzoimidazol-2-one;
5-Fluoro-1-(3-[4-(4-fluoro-phenyl)-piperazin-1-yl]-2-hydroxy-propyl)-1,3-dihydro -benzoimidazol-2-one;
1-Benzoimidazol-1-yl-3-[4-(3-methoxy-phenyl)-piperazin-1-yl]-propan-2-ol;
1-Benzoimidazol-1-yl-3-[4-(4-methoxy-phenyl)-piperazin-1-yl]propan-2-ol;
1-Benzoimidazol-1-yl-3-(4-phenyl-piperazin-1-yl)-propan-2-ol;
1-{4-[4-(3-Benzoimidazol-1-yl-2-hydroxy-propyl)-piperazin-1-yl]-phenyl}-ethanone;
1-(4Benzo[1,3]dioxol-5-ylmethyl-piperazin-1-yl)+benzoimidazol-1-yl-propan-2-ol;
1-Benzoimidazol-1-yl-3-[4-(3,4-dimethyl-phenyl)-piperazin-1-yl]-propan-2-ol;
4-[4-(3-Benzoimidazol-1-yl-2-hydroxy-propyl)-piperazin-1-yl]-phenol;
1-Benzoimidazol-1-yl-3-(4-phenethyl-piperazin-1-yl)-propan-2-ol;
1-Benzoimidazol-1-yl-3-[4-(3-phenyl-allyl)-piperazin-1-yl)]propan-2-ol;
1-Benzoimidazol-1-yl-3-[4-(3-chloro-propyl)-piperazin-1-yl]-propan-2-ol;
2-[4-(3-Benzoimidazol-1-yl-2-hydroxy-propyl)-piperazin-1-yl-1-morpholin-4-yl -ethanone;
1-(4-Benzhydryl-piperazin-1-yl)-3-benzoimidazol-1-yl-propan-2-ol;
1-Benzoimidazol-1-yl-3-{4-[bis-(4-fluoro-phenyl)-methyl]-piperazin-1 -yl}-propan-2-ol;
1-Benzoimidazol-1-yl-3-[4-(4-nitro-phenyl)-piperazin-1-yl]-propan-2-ol;
4-(3-Benzoimidazol-1-yl-2-hydroxy-propyl)-piperazine-1-carboxylic;

5-Fluoro-1-{3-[4-(4-fluoro-phenyl)-piperazin-1-yl]-propyl}-1H-benzoimidazole;

3-[4-(3-Benzoimidazol-1-yl-2-hydroxy-propyl)-piperazin-1-yl]-1-yl]-1-phenyl-propan-1-one;

4-[4(3-Benzoimidazol-1-yl-2-hydroxy-propyl)-piperazin-1-yl]-1-(fluoro-phenyl)-butan-1-one;

1-Benzoimidazol-1-yl-3-[4-(tetrahydro-furan-2-ylmethyl)-piperazin-1-yl]-propan-2-ol;

[4-(3-Benzoimidazol-1-yl-2-hydroxy-propyl)-piperazin-1-yl]-(tetrahydro-furan-2-yl)-methanone;

[4-(3-Benzoimidazol-1-yl-2-hydroxy-propyl)-piperazin-1-yl]-(2,3-dihydro-benzo[1,4]dioxin-2-yl)-methanone;

1-Benzoimidazol-1-yl-3-[4-(2,3-dihydro-benzo[1,4]dioxin-2-ylmethyl)-piperazin-1-yl]-propan-2-ol;

1-Benzoimidazol-1-yl-3-[4-2-nitro-butyl)-piperazin-1-yl]-propan-2-ol;

3-[4-(3-Benzoimidazol-1-yl-2-hydroxy-propyl)-piperazin-1-yl]-1-(4-chloro-phenyl)-propan-1-one;

1-Benzoimidazol-1-yl-3-[4(5,5-diphenyl-pent-en-1-yl)-piperazin-1-yl]-propan-2-ol; 5,6-Difluoro-1-{3-[4-(4-fluoro-phenyl)-piperazin-1-yl]-propyl}-1H-benzoimidazol;

1-[3-(4-Benzyl-piperazin-1-yl)-propyl]-5-fluoro-2-methyl-1H-benzoimidazole;

1-[3-(4-Benzo[1,3]dioxol-5-ylmethyl-piperazin-1-yl)-propyl]-5-fluoro-2-methyl-1 H-benzoimidazole;

1-{3-[-4(3-Chloro-5-trifluoromethyl-pyridin-2-yl)-piperazin-1-yl]-propyl}-5-fluoro-2methyl-1H-benzoimidazole;

1-[3-(5-Fluoro-2-methyl-benzoimidazol-1-yl)-propyl](4-fluoro-phenyl)-piperidin-4-ol;

1-{3-[4-(4-Chloro-phenyl)-3,6-dihydro-2H-pyridin-1-yl]-propyl}-5-fluoro-2-methyl-1H-benzoimidazole;

1-{3-[4-(3,5-Dichloro-pyridin-2-yl)-piperazin-1-yl]-propyl}-5-fluoro-2-methyl 1H-benzoimidazole;

5-Fluoro-2-methyl-1-[3-(4-phenyl-piperazin-1-yl)-propyl]-1H-benzoimidazole;

2-[3-(5-Fluoro-2-methyl-benzoimidazol-1-yl-propyl]-2,3,4,9-tetrahydro-1H-arboline;

1-{3-[4-(6-Chloro-pyridazin-3-yl)-piperazin-1-yl]-propyl}-5-fluoro-2-methyl-1 H-benzoimidazole;

1-{3-[4-(2-Chloro-phenyl)-piperazin-1-yl]-propyl}-5-fluoro-2-methyl-1H-benzoimidazole;

6,7-Difluoro-1-{3-[4-(4-fluoro-phenyl)-3,6-dihydro-2H-pyridin-1-yl]-propyl}-2-methyl-1H-benzoimidazole;

3-[3-(5-Fluoro-2-methyl-benzoimidazol-1-yl)-propyl]-2,3,4,4a,5,6-hexahydro-1H-pyrazino[1,2-a]quinoline;

1-{3-[4-(4-Chloro-phenyl)-3,6-dihydro-2H-pyridin-1-yl]-propyl}-6,7-difluoro-2-methyl-1H-benzoimidazole;

5-Fluoro-1-{3-[4-(5-fluoro-pyrimidin-2-yl)-piperazin-1-yl]-propyl}-2-methyl-1 H-benzoimidazole;

5,6-Difluoro-1-{3-[4-(4-fluoro-phenyl)-3,6-dihydro-2H-pyridin-1-yl]-propyl}-2-methyl-1H-benzoimidazole;

5-Fluoro-1-{3-[4-(4-fluoro-phenyl)-piperazin-1-yl]-2,2-dimethyl-propyl}-2-methyl-1H-benzoimidazole;

Acetic acid 2-(5-fluoro-2-methyl-benzoimidazol-1-yl)-1-[4-(4-fluoro-phenyl)-pererazin-1-ylmethyl]-ethyl ester;

1-(5-Fluoro-2-methyl-benzoimidazol-1-yl)-3-[4-(4-fluoro-phenyl)-piperazin-1-yl]-propan-2-ol;

5-Fluoro-1-{3-[4-(4-fluoro-phenyl)-piperazin-1-yl]-2-methyl-propyl}-2-methyl-1H-benzoimidazole;

5-Fluoro-1-{3-[4-(4-fluoro-phenyl)-piperazin-1-yl]-2-methoxy-propyl}-2-methyl-1H-benzoimidazole;

5-Fluoro-1-{3-[4-(4-fluoro-phenyl)-3,6-dihydro-2H-pyridin-1-yl]-propyl}-2-trifluoromethyl-1H-benzoimidazole;

5-Fluoro-1-{3-[4-(4-fluoro-phenyl)-piperazin-1-yl]-3-methyl-butyl}-2-methyl-1-benzoimidazole;

5-Fluoro-1-{3-[4-(4-fluoro-phenyl)-piperazin-1-yl]-propyl}-2-trifluoromethyl-1H-benzoimidazole;

5-Fluoro-1-{3-[4-(4-fluoro-phenyl)-piperazin-1-yl]-butyl}-2-methyl-1H-benzoimidazole; and 5-Fluoro-1-{3-[4-(4-fluoro-phenyl)-piperazin-1-yl]-butyl}-2-methyl-1H-benzoimidazole.

Other embodiments of this invention include:

(a) compounds of the formula I wherein $R^1$ is phenyl and is either unsubstituted or substituted with one or two substituents selected from halo, $(C_1-C_6)$alkyl substituted with from one to three fluorine atoms, $(C_1-C_6)$alkoxy substituted with from one to three fluorine atoms, cyano, —C(=O)$R^8$, aryl and heteroaryl;

(b) compounds of the formula I wherein $R^1$ is indanyl and is either unsubstituted or substituted with one or two substituents selected from halo, $(C_1-C_6)$alkyl substituted with from one to three fluorine atoms, $(C_1-C_6)$alkoxy substituted with from one to three fluorine atoms, cyano, —C(=O)$R^8$, aryl and heteroaryl;

(c) compounds of the formula I wherein $R^1$ is naphthyl and is either unsubstituted or substituted with one or two substituents selected from halo, $(C_1-C_6)$alkyl substituted with from one to three fluorine atoms, $(C_1-C_6)$alkoxy substituted with from one to three fluorine atoms, cyano, —C(=O)$R^8$, aryl and heteroaryl;

(d) compounds of the formula I wherein Rhu 1is heteroaryl and is either unsubstituted or substituted with one or two substituents selected from halo, $(C_1-C_6)$alkyl substituted with from oneto three fluorine atoms, $(C_1-C_6)$alkoxy substituted with from one to three fluorine atoms, cyano, —C(=O)$R^8$, aryl and heteroaryl;

(e) compounds of the formula I wherein $R^5$, $R^6$ and $R^7$ are independently selected from $(C_1-C_6)$alkyl optionally substituted with from one to three fluorine atoms, $(C_1-C_6)$alkoxy optionally substituted with from one to three fluorine atoms, cyano and halo;

(f) compounds of the formula I wherein $R^4$ is hydrogen;

(g) compounds of the formula I wherein $R^4$ is $(C_1-C_6)$alkyl;

(h) compounds of the formula I wherein $R^4$ is amino;

(i) compounds of the formula I wherein $R^4$ is —NH$R^{10}$;

(j) compounds of the formula I wherein $R^4$ is S$R^{10}$;

(k) compounds of the formula I wherein $R^4$ is —O$R^{10}$;

(l) compounds of the formula I wherein $R^4$ is hydroxy;

(m) compounds of the formula I wherein $R^{11}$ is absent;

(n) compounds of the formula I wherein $R^2$ and $R^3$ are both hydrogen;

(o) compounds of the formula I wherein one or both of $R^2$ and $R^3$ are hydroxy;

(p) compounds of the formula I wherein $R^2$ and $R^3$ together form an oxo group;

(q) compounds of the formula I wherein one of $R^2$ and $R^3$ is $(C_1-C_6)$alkyl;

(r) compounds of the formula I wherein X is carbon;

(s) compounds of the formula I wherein X is nitrogen;

(t) compounds of the formula I wherein $R^4$ is oxygen; and (v) compounds of the formula I wherein $R^4$ is sulfur.

The compounds of formula I above may contain chiral centers and therefore may exist in different enantiomeric forms. This invention relates to all optical isomers and all other stereoisomers of compounds of the formula I and mixtures thereof.

This invention also relates to a pharmaceutical composition for treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an amount of a compound of the formula I, or pharmaceutically acceptable salt thereof, that is effective in treating or preventing such condition, and a pharmaceutical acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising administering to said mammal an amount of a compound of the formula I, or pharmaceutically acceptable salt thereof, that is effective in treating or preventing such condition.

The present invention also relates to a pharmaceutical composition for treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure; chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising a dopaminergic effective amount of a compound of the formula 1, or a pharmaceutical acceptable salt thereof, and a pharmaceutically acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an administering to said mammal a dopaminergic effective amount of a compound of the formula 1, or pharmaceutically acceptable salt thereof.

This invention also relates to a pharmaceutical composition for treating or preventing a disease or condition, the treatment or prevention of which can be effected or facilitated by altering (i.e., increasing or decreasing) dopamine mediated neurotransmission in a mammal, including a human, comprising a dopaminergic effective amount of a compound of the formula I, or a pharmaceutically acceptable salt thereof, and a pharmaceutically acceptable carrier.

This invention also relates to a method of treating or preventing a disease or condition, the treatment or prevention of which can be effected or facilitated by altering (i.e., increasing or decreasing) dopamine mediated neurotransmission in a mammal, including a human, comprising administering to said mammal a dopaminergic effective amount of a compound of the formula 1, or a pharmaceutically acceptable salt thereof.

The present invention also relates to a pharmaceutical composition for treating or preventing a condition selected from sleep disorders, sexual disorders (including sexual. dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising a D4 receptor binding effective amount of a compound of the formula I, or a pharmaceutical acceptable salt thereof, and a pharmaceutically acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an administering to said mammal a D4 receptor binding effective amount of a compound of the formula 1, or pharmaceutically acceptable salt thereof.

This invention also relates to a pharmaceutical composition for treating or preventing a disease or condition, the treatment or prevention of which can be effected or facilitated by altering dopamine mediated neurotransmission in a mammal, including a human, comprising a D4 receptor binding effective amount of a compound of the formula I, or a pharmaceutically acceptable salt thereof, and a pharmaceutically acceptable carrier.

This invention also relates to a method of treating or preventing a disease or condition, the treatment or prevention of which can be effected or facilitated by altering dopamine mediated neurotransmission in a mammal, including a human, comprising administering to said mammal a D4 receptor binding effective amount of a compound of the formula I, or a pharmaceutically acceptable salt thereof.

The term "dopaminergic effective amount", as used herein, refers to an amount of a compound sufficient to inhibit the binding of dopamine to a dopamine receptor with the effect of altering (i.e., increasing or decreasing) dopamine mediated neurotransmission.

DETAILED DESCRIPTION OF THE INVENTION

The preparation of compounds of the formula I are described below. In the reaction schemes and discussion that follows, X, $R^1$, through $R^{15}$, $R^{15}$ through $R^{17}$ and the dotted lines in all formulae are defined as above.

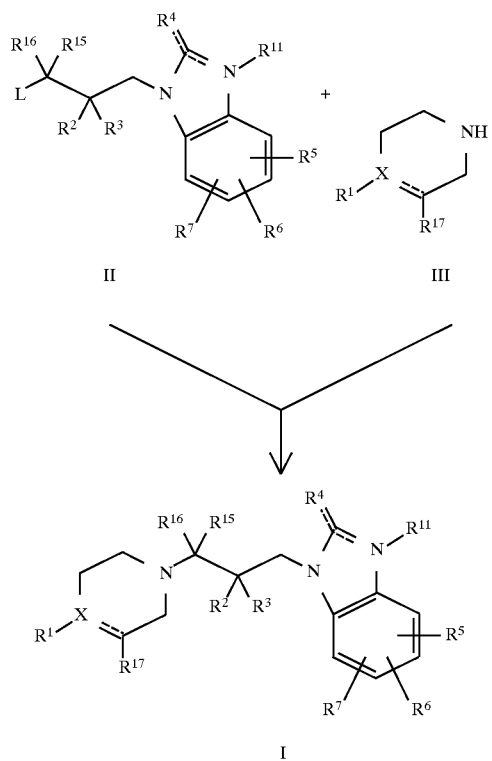

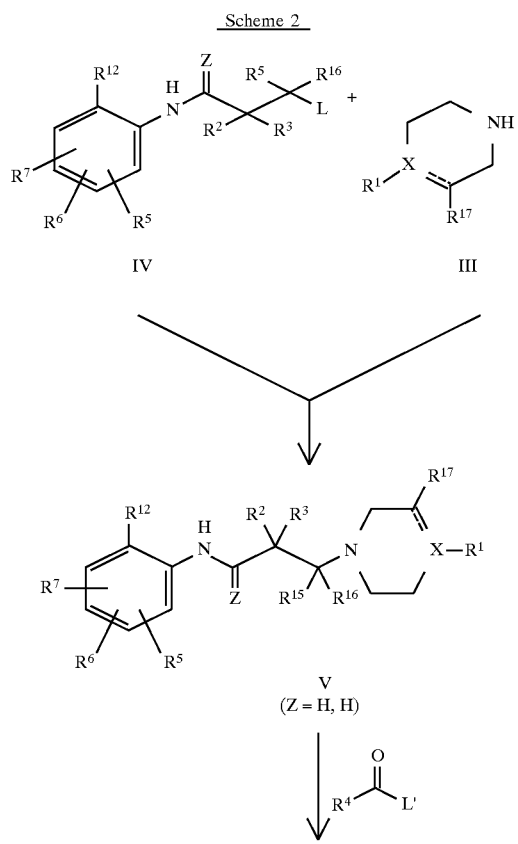

Scheme 2
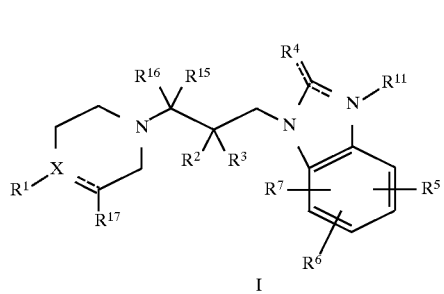
I
Scheme 3
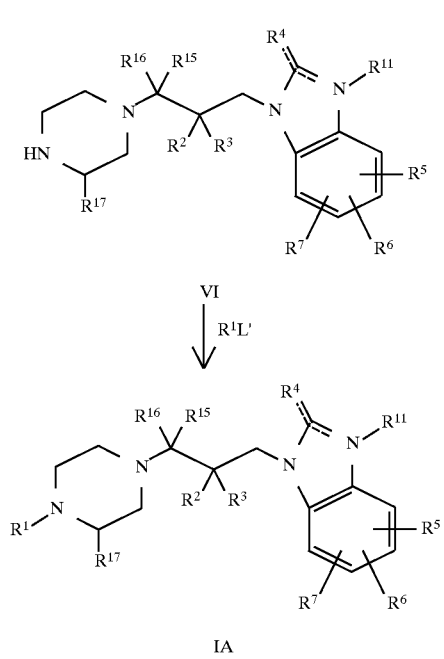
Scheme 4
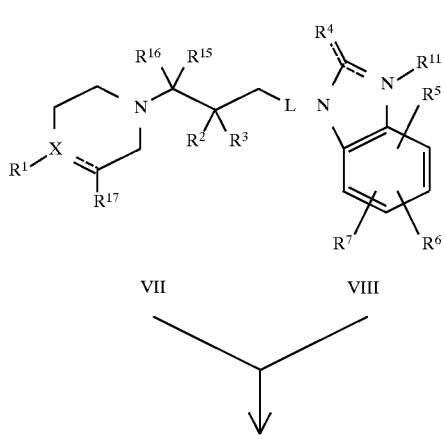
Scheme 4
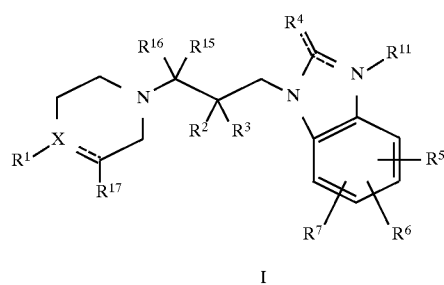
I
Scheme 5
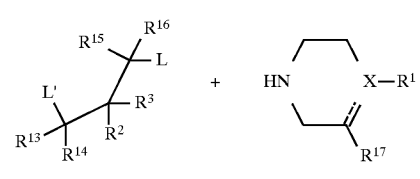
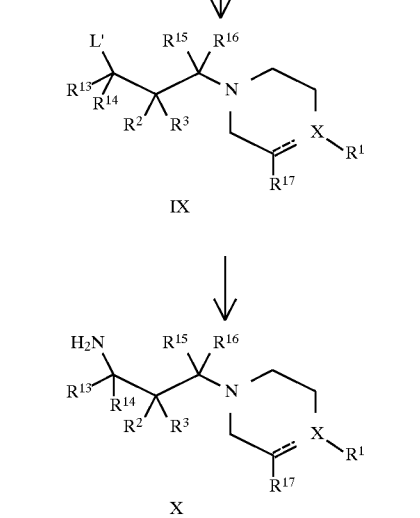

-continued
Scheme 5

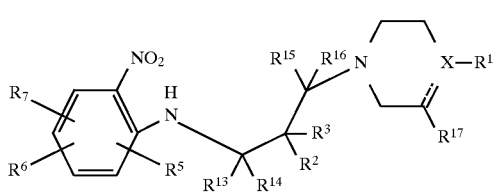

V'

↓

I ($R^{13}$ and $R^{14}$ = hydrogen)

Scheme 6

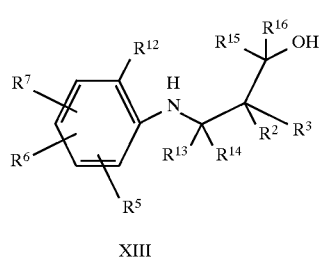

XIII

↓

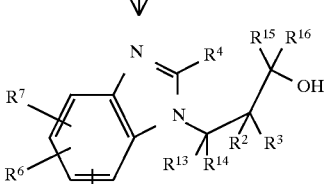

XIV

↓

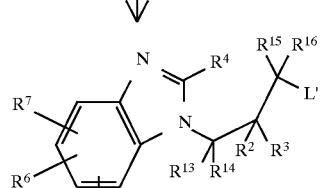

XIVA

↓

-continued
Scheme 6

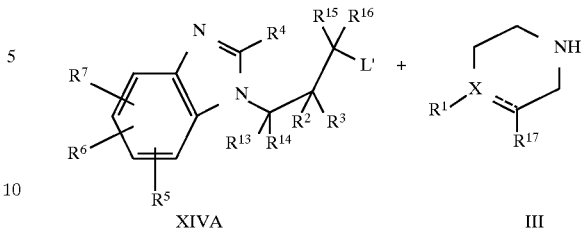

XIVA      III

↓

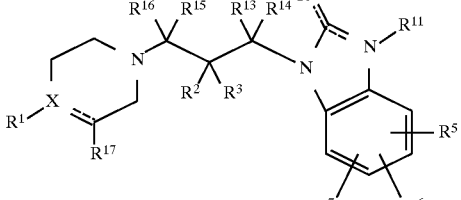

I ($R^{13}$ and $R^{14}$ = hydrogen)

Referring to scheme 1, a compound of the formula II wherein L is a leaving group is reacted with a compound of the formula III to form the corresponding compound of formula I. Suitable leaving groups include chloro, bromo, iodo, —O—($C_1$–$C_6$)—alkylsulfonyl and —O—arylsulfonyl (e.g., —O—phenylsulfonyl, —O—naphthylsulfonyl or —O—paranitrophenylsulfonyl). Also, one of $R^2$ and $R^3$ in compound II may be oxygen and may, together with the carbon to which it is attached and L, form an epoxy group, while the other of $R^2$ and $R^3$ in such a case is selected from the values given above for these substituents. This reaction is generally carried out in an inert polar solvent such as a lower alcohol, a cyclic or acyclic alkylketone (e.g., ethanol or acetone), an alkylester (e.g., ethylacetate), a cyclic or acyclic mono or dialkylamide (e.g., N-methylpyridin 2-one or dimethylformamide (DMF)), a cyclic or acyclic alkyl ether (e.g., tetrahydrofuran (THF) or diisopropyl ether) or a mixture of two or more of the foregoing solvents, at a temperature from about 0° C. to about 150° C. It is preferably carried out in ethanol at a temperature from about 0° C. to about the reflux temperature of the solvent. The presence of an acid acceptor such as an alkali carbonate or tertiary amine may be useful.

Referring to scheme 2, compounds of the formula I may also be prepared in the following manner. A compound of the formula IV wherein $R^{12}$ is selected from $NO_2$, $NH_2$, ureido, thiouriedo and —NH(C=O)—Q, wherein Q is hydrogen, ($C_1$–$C_4$)alkyl, aryl or heteroaryl, wherein aryl and heteroaryl are defined as in the definition of $R^1$ above, Z represents one oxygen atom or two hydrogen atoms (each single bonded to the carbon to which Z is attached) and L represents a suitable leaving group, as defined above, is reacted with a compound of the formula III to form an intermediate compound of the formula V. This reaction is typically carried out in an inert polar solvent such as those described above for the reaction of scheme 1, at a temperature from about 0° C. to about 150° C. The preferred solvent is ethanol and the preferred temperature is from about 0° C. to about the reflux temperature of the solvent. As with the reaction of scheme 1, the addition of acid acceptors such as alkali carbonates and tertiary amines may be useful.

Intermediates of the formula V wherein Z is oxygen must be converted into the corresponding compounds wherein Z is (H, H). This can be accomplished using any of several standard methods of reduction that are well known in the art, e.g., by reacting the compound of formula V wherein Z is oxygen with a solution of lithium aluminum hydride in THF (preferably containing five molar equivalents) in a THF solvent.

The intermediate of formula V wherein Z is (H, H) may be converted, either in situ or after isolation, into the corresponding compound of formula I by reacting it with a compound of the formula $R^4$—C(=O)—L' wherein L' is an appropriate leaving group (e.g., chloro, bromo, iodo, fluoro, amino, —O—($C_1$–$C_6$)alkylsulfonyl or O-arylsulfonyl, wherein aryl is selected from phenyl, naphthyl and paranitrophenyl) and an optional dehydrating reagent. Suitable solvents for this reaction include inert polar solvents such as cyclic and acyclic alkyl ethers (e.g., diisopropyl ether and THF), alkylesters (e.g., ethylacetate), cyclic and acyclic alkylketones (e.g., ethanol and acetone), pyridine derivatives (e.g., lutidine and collidine), halogenated solvents (e.g., methylene chloride and dichloroethane) and cyclic, acyclic N-,N-dialkyl alkylamides (e.g., DMF and N-methyl -2-pyrrolidinone (NMP), and acyclic alkylamides (e.g., formamide or acetamide). The reaction temperature may range from about 0° C. to about 150° C. Preferably, the reactants (V and $R^4$—C(=O)—L') are initially reacted at about 0° C. and slowly brought to about the reflux temperature of the reaction mixture. The addition of acid acceptors such as alkali carbonates and tertiary amines may be useful. Addition of a dehydrating agent may also be useful.

Scheme 3 illustrates a method of preparing compounds of the formula I wherein X is nitrogen and $R^1$ is other than hydrogen. These compounds are referred to in scheme 3 and hereinafter as "compounds of the formula IA." Referring to scheme 3, such compounds can be prepared by reacting the corresponding compounds in which $R^1$ is hydrogen, with a compound of the formula $R^1$ L' wherein R' is other than hydrogen and L' is a suitable leaving group, as defined above. Suitable solvents for this reaction include cyclic and acyclic mono and dialkylamides (e.g., DMF or N-methyl-2-pyrrolidinone), and lower alcohols, and mixtures of two or more solvents from the foregoing classes. Ethanol and N-methyl-2-pyrrolidinone are preferred solvents. The reaction temperature may range from about 0° C. to about 150° C., and is preferably between about 0° C. and the reflux temperature of the solvent. Addition of an acid acceptor such as an alkali metal carbonate or a tertiary amine may be useful.

An alternate method of preparing compounds of the formula I is illustrated in scheme 4. Referring to scheme 4, a compound of the formula VII, wherein L is a leaving group, is reacted with a compound of the formula VII to yield a compound of the formula 1. Examples of appropriate leaving groups are chlorine, bromino, iodo, —O—($C_1$–$C_6$) alkylsulfonyl and —O—arylsulfonyl wherein aryl may be, for example, phenyl, naphthyl or paranitrophenyl. Also, one of $R^2$ and $R^3$ in formula VII can be oxygen and may form, together with the carbon to which it is attached and L, an epoxy group. In such a case, the other of $R^2$ and $R^3$ is selected from the values given above in the definitions of these substituents. This reaction is generally carried out using the similar solvents and under similar conditions to those described above for the reaction of scheme 3.

Compounds of the formula 11 are either commercially available or can be prepared by methods well known to those skilled in the art from compounds of the formula IV. The preparation of a compound of the formula 11 from a compound of the formula IV is exemplified in Example 2.

Compounds of the formula IV can be prepared by procedures similar to those described in the following literature references: *J. Org. Chem.* 38, 3498–502 (1973) and *J. Chem. Soc.* (C). 2364–66 (1971). The synthesis of compounds of the formula IV may be accomplished, for example, by reacting a known aniline derivative containing an $R^{12}$ substituent in the ortho position with a substituted or unsubstituted propyl group transferring agent. Such a synthesis is described in Example 8.

Compounds of the general formula III where X is nitrogen may be prepared by reacting commercially available piperazine with aryl transferring reagents such as, for example, 4-nitro fluorobenzene, 2-nitro fluorobenzene or similar reagents followed by well known procedures allowing the exchange of the nitro group against other substituents. Compounds of the general formula III where X is nitrogen may also be prepared by reacting commercially available piperazine with heteroaryl transferring reagents such as, for example, 2-chloro or 2-S-methyl mercapto pyrimidine derivatives, 2-chloro- or 2-bromo pyridine derivatives, 2-chloro or 2-fluoro pyridazine derivatives, 3-chloro isobenzothiazole derivatives, 3-chloro isobenzooxazole derivatives, 3-chloro indazole derivatives or similar reagents. These reactions are preferably carried out in the form of mixtures containing, if desired, combinations of cyclic and acyclic mono and dialkylamides and ($C_1$–$C_4$) alcohols or inert organic solvents such as cyclic and acyclic alkyl ethers (e.g., diethyl ether and THF), cyclic and acyclic alkyl esters (e.g., ethylacetate and gama butyrolactones), cyclic and acyclic alkylketones (e.g., acetone and cyclohexanone), pyridine derivatives or halogenated solvents, at temperatures ranging from about 0° C. to about 150° C., preferable at a temperature from about 0° C. to about the reflux temperature of the reaction mixture. Addition of acid acceptors such as an alkali carbonates, tertiary amines or similar reagents, as well as the addition of dehydrating reagents, may be useful.

Compounds of the formula IIII wherein X is carbon may be prepared by reacting commercially available 4-piperidinone with aryl transferring reagents such as, for example, aryl grignards or similar reagents and by dehydrating the corresponding benzyl alcohol intermediates. Compounds of the general formula III wherein X is CH may be prepared by reacting commercially available 4-piperidinone with aryl transferring reagents such as, for example, aryl grignards or similar reagents and by hydrogenating the corresponding benzyl alcohol intermediates with either platinum dioxide or palladium on carbon.

Compounds of general structure VI may be prepared by reacting compounds of the general formula II with piperazine or 1-t-butoxycarbonyl piperazine, as exemplified in Example 9, preferably in the form of a mixture containing combinations of ($C_1$–$C_4$) alcohols, cyclic and acyclic mono and dialkylamides or inert organic solvents such as cyclic and acyclic alkyl ethers, cyclic and acyclic alkyl esters, cyclic and acyclic alkylketones, pyridine derivatives or halogenated solvents at temperatures ranging from about 0° C. to about 150° C., preferable from about at 0° C. to the reflux temperature of the solvent mixture. Addition of acid acceptors such as an alkali carbonates, tertiary amines or similar reagents may be useful. Corresponding piperazine intermediates (having different substitution pattern) can be formed by reacting the products of the foregoing reaction with an appropriate aryl transferring reagent such as, for example, 4-nitro fluorobenzene, 2-nitro fluorobenzene or similar reagents followed by well known procedures allowing the exchange of the nitro grouping against other substituents. Such corresponding piperazine intermediates can also be prepared by reacting other intermediates with heteroaryl transferring reagents such as for example, 2-chloro or 2-S -methyl mercapto pyrimidine derivatives, 2-chloro or 2-bromo pyridine derivatives, 2-chloro or 2-fluoro pyridazine derivatives, 3-chloro isobenzothiazole derivatives, 3-chloro isobenzooxazole derivatives, 3-chloro indazole derivatives or similar reagents. The preferred conditions for these reactions are similar to those described in Example 11.

Similarly, compounds of the formula VII may be prepared by reacting compounds of the formula III with compounds of the general formula $L^2$—$CH_2$—$C(R^2(R^3$—$CH_2$—$L^3$, wherein each of $L^2$ and $L^3$ is a leaving group that is, for example, independently selected from chloro, bromo, iodo, O-alkylsulfonyl and O-arylsulfonyl, wherein aryl may be, for example, phenyl, naphthyl or paranitrophenyl. Also, one of $R^2$ and $R^3$ in the above compound may be oxygen and may, together with the carbon to which it is attached and $L^2$ or $L^3$, form an epoxy group, while the other of $R^2$ and $R^3$, in such a case, is selected from the values given above for those substituents. The reaction mixture may contain one or more of inert organic solvents such as cyclic and acyclic alkyl ethers, cyclic and acyclic alkyl esters, cyclic and acyclic alkylketones, pyridine derivatives, halogenated solvents or cyclic and acyclic N—,N-dialkylalkylamides. The reaction temperature may range from about 0° C. to about 150° C. The reaction is preferable carried out at a temperature from about 0° C. to about the of the reflux temperature of the reaction mixture. Addition of an acid acceptor such as an alkali carbonate, a tertiary amine or a similar reagent may be useful.

Compounds of the formula VII may be prepared according to methods known in the literature, such as, for example, as described in *J. Chem. Soc.*, p. 1396 (1949), *Synth. Commun.*, 5, p. 461 (1975), *J. Amer. Chem. Soc.*, 73, p. 4297 (1951) or *J. Chem. Soc.*, 39, p. 3155 (1951).

Scheme 5 illustrates an alternate procedure for preparing compounds of the formula I. Referring to scheme 5, compounds of the formula IX may be prepared according to methods known in the literature, such as, for example, as described in the following references: *J. Chem. Soc.*, pp. 1396 (1949); *Synth. Commun.*, 5, pp. 461 (1975); *J. Amer. Chem. Soc.*, 73, pp. 4297 (1951); and *J. Chem. Soc.*, 39 pp. 3155 (1951). They may also be prepared, as shown in scheme 5, by reacting an otherwise optionally substituted $C_3$–$C_4$ alkyl derivative of the formula XI with a compound of the formula III. In structure XI, L and L' are defined as above and L' may optionally be a nitro group or a protected amino group when $R^{13}$ and $R^{14}$ are both hydrogen; $R^2$ and $R^3$ are defined as above and one of $R^2$ and $R^3$ may be oxygen and may, together with the carbon to which it is attached and either L or L', form an epoxy group; and $R^{13}$ and $R^{14}$ are both hydrogen except that the —$CL'R^{13}R^{14}$ moiety may optionally be a cyano group (i.e., wherein L' is nitrogen and $R^{13}$ and $R^{14}$ represent bonds rather than radicals).

These reactions can be carried out conveniently in solvents such as alcohols, cyclic and acyclic alkylketones, cyclic and acyclic alkylesters, cyclic and acyclic mono and dialkylamides, acetonitrile and cyclic and acyclic alkyl ethers, or mixtures of such solvents, at a temperature from about 0° C. to about 150° C., preferably about 0° C. or the reflux temperature of the solvent. The presence of an acid acceptor such an alkali carbonate, tertiary amine or a similar reagent may be useful.

For all structures depicted in schemes 5 and 6, $R^{13}$ and $R^{14}$ are defined as above. Thus, for all such structures that do not contain the moiety —$CL'R^{13}R^{14}$, both $R^{13}$ and $R^{14}$ are hydrogen.

Alternatively, compounds of the general formula IX can be prepared from compounds of the general formula XI, as defined above, by reacting the latter compounds with a compound of the formula

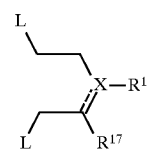

XVI wherein L is defined as above provided that at least one of said L is an amino or protected amino group. Appropriate and preferred solvents and conditions for this reaction are similar to those described above or the reaction of compounds of the formulae Xl and III.

Compounds of the formula XVI can be prepared by a procedures analogous to that of Example 23A.

Compounds of the formula IX can be converted into the corresponding compounds of formula X as follows. When L' is a protected amino group, (for example, when the nitrogen protecting group is benzyl, benzyloxycarbonyl, t-butoxycarbonyl or trityl), the protecting group can be removed using either hydrogenation or acidic deprotection conditions. When L' is an amino group protected by a phthalimido group, the protecting group may be conveniently removed using standard hydrogenation conditions. When L' is a nitro group, the compound of formula X may be formed by reducing the compound of formula IX using conventional reduction methods. For example, the reduction can be accomplished using a hydride reagent such as lithium aluminum hydride or borane, or using hydrogen gas in the presence of catalyst such as Raney nickel, platinum oxide, palladium/carbon or another appropriate catalyst.

When the —$CL'R^{13}R^{14}$ moiety is a cyano group, it can be reduced to a —$CH_2NH_2$ group using, for example, a hydride reagent such as lithium aluminum hydride or sodium borohydride in the presence of cobalt chloride, or using other conventional methods known to those skilled in the art.

Reaction of the resulting compound of the formula X with a compound of the formula XII, wherein L" is defined as L' above, as shown on the second page of scheme 5, yields a compound of the formula V wherein $R^{12}$ is nitro (referred to in scheme 5 and hereinafter as a compound of the formula V'), which can then be converted into the corresponding compound of the formula I wherein $R^4$ is methyl or trifluoromethyl by reducing the nitro group. This can be accomplished using a metal such as zinc or tin in acetic acid or trifluoroacetic acid, containing, if desired, the corresponding acid anhydride. In the case of compounds of the formula V' containing hydroxy substituents, an ester intermediate may be formed, which can then be converted into the corresponding hydroxy substituted compound of the formula I using conventional methods known to those skilled in the art. For example, such esters can be treated with an aqueous alkali hydroxide solution in an appropriate solvent selected from cyclic and acyclic mono and dialkylamides and $C_1$–$C_4$ alcohols and mixtures thereof at a temperature from about 0° C. to about 150° C., preferably from about 0° C. to about the reflux temperature. The hydroxy substituted compounds of the formula I can be converted into the corresponding alkoxy substituted compounds by treating them first with an alkali hydride such as sodium hydride or calcium hydride, using solvents and conditions as described immediately above, and then with an alkylating agent such as, for example, methyl iodide, dimethylsulfate, allyl iodide, ethyl iodide or a similar reagent. Scheme 6 illustrates the preparation of compounds of the formula I starting with the hydroxy derivatives of formula XII. The starting materials of formula XIII wherein $R^{12}$ is nitro may be prepared by reacting a compound of the formula Xl wherein L is hydroxy and L' is amino with a compound of the formula XII, as defined above and depicted in scheme 5. This reaction is generally carried out using similar solvents and conditions to both specified for the reaction of scheme 1.

Compounds of the formula Xil wherein $R^{12}$ is nitro may be converted into the corresponding compounds of the formula XIII wherein $R^{12}$ is amino using conventional reduction methods such as, for example, using a mixture of a metal such as zinc or tin and hydrochloric acid or, alternatively, using a hydride donating reagent such as, for example, lithium aluminum hydride or borane, or hydrogenating the reactant of formula XIII in the presence of a catalyst such as Raney nickel, platinum oxide or palladium/carbon.

Compounds of the formula XIII wherein $R^{12}$ is nitro can be converted into the corresponding compounds of formula XIV wherein $R^4$ is methyl or trifluoromethyl by reducing the nitro group with a metal such as zinc or tin in acetic acid or trifluoroacetic acid containing, if desired, the corresponding acid anhydride. This reaction produces an ester intermediate which can then be converted into compounds of the formula XIV using standard methods known to those skilled in the art. For example, the esters can be treated with an aqueous alkali hydroxide solution in an appropriate solvent selected from cyclic and acyclic mono and dialkylamides and $C_1$–$C_4$ alcohols, at temperatures from about 0° C. to about 150° C., preferably from about 0° C. to about the reflux temperature.

Alternatively, compounds of the formula XIV wherein $R^4$ is an alkyl group may be prepared by reacting the appropriate compounds of the formula Xil wherein $R^{12}$ is amino with an acylating agent such as propionyl chloride, isopropionyl bromide, acetic acid/formic acid anhydride, ethyl formate or a similar reagent, and then treating the intermediary product formed with an aqueous solution of an acid such as hydrochloric acid, trifluoroacetic acid or methanesulfonic acid, preferably hydrochloric acid at a temperature ranging from about 0° C. to about the boiling point of the acid.

Compounds of the formula XIV wherein $R^4$ is methyl or trifluoromethyl may be converted into compounds of the formula XIVA wherein L' is a leaving group such as chloro, bromo, iodo, O-alkylsulfonyl or O-arylsulfonyl, wherein aryl may be, for example, phenyl, naphthyl, or paranitrophenyl, by reacting them with an alkyl or arylsulfonylchloride in an appropriate solvent such as one selected from cyclic and acyclic mono and dialkylamides, chloroform, methylene chloride and pyridine and mixtures of the foregoing solvents at a temperature ranging from about –25° C. to about 25° C., preferably at about –25° C., in presence of an acid acceptor an such as an alkali carbonate, a tertiary amine or a similar reagent. When L' in the desired compound of formula XIVA is chloro, bromo or iodo, the corresponding compound of formula XIV wherein $R^4$ is methyl or trifluoromethyl is reacted with the appropriate phosphoryl or thionyl halide in a solvent such as chloroform, methylene chloride, benzene, toluene or mixtures thereof, at a temperature ranging from about 0° C. to about the reflux temperature of the reaction mixture, preferably at the reflux temperature.

Compounds of the formula XIVA wherein $R^4$ is methyl or trifluoromethyl and L' is a leaving group such as, for example, chloro, bromo, iodo, O-alkylsulfonyl and O-arylsulfonyl, wherein aryl may be, for example, phenyl, naphthyl, or parantitrophenyl, can be converted into compounds of the formula I by reacting said compound XIVA with a compound of general formula III, using similar solvents and conditions to those specified for the reaction shown in scheme 1.

These reactions can conveniently carried out in solvents such as alcohols, cyclic and acyclic alkylketones, cyclic and acyclic alkylesters, cyclic and acyclic mono and dialkylamides, acetonitrile, and cyclic and acyclic alkyl ethers at a temperature ranging from 0° C. to 150° C., preferable at 0° C. or the boiling point of the same solvent. The presence of an acid acceptor such as an alkali carbonate, a tertiary amine or similar reagents may be useful.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 4 atmospheres are generally acceptable, and ambient pressure, i.e., about 1 atmosphere, is preferred as a matter of convenience.

The novel compounds of the formula I and the pharmaceutically acceptable salts thereof (hereinafter "the therapeutic compounds of this invention") are useful as dopaminergic agents, i.e., they possess the ability to alter dopamine mediated neurotransmission in mammals, including humans. They are therefore able to function as therapeutic agents in the treatment of a variety of conditions in mammals, the treatment or prevention of which can be effected or facilitated by an increase or decrease in dopamine mediated neurotransmission. Such conditions include sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol addictions, vascular and cardiovascular disorders, ocular disorders (including glaucoma), dystonia, tardive dyskinesia, Gilles De LaTourette's syndrome and other hyperkinesias, dementia, ischemia, Parkinson's disease, movement disorders such as akathesia, hypertension and diseases caused by a hyperactive immune system such as allergies and inflammation.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g., through the use of a patch), parenterally or topically. Oral administration is preferred. In general, these compounds are most desirably administered in dosages ranging from about 0.01 mg up to about 250 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The D4 dopaminergic activity of the compounds of the present invention may be determined by the following procedure.

The determination of D4 dopaminergic activity has been described by Van Tol et al., Nature, vol. 350, 610 (London, 1991). Clonal cell lines expressing the human dopamine D4 receptor are harvested and homogenized (teflon pestle) in a 50 mM Tris.HCl (pH 7.4 at 4° C.) buffer containing 5 mM EDTA, 1.5 mM calcium chloride ($CaCl_2$), 5 mM magnesium chloride ($MgCl_2$), 5 mM potassium chloride (KCl) and 120 mM sodium chloride (NaCl). The homogenates are centrifugated for 15 min. at 39,000 g, and the resulting pellets resuspended in a buffer at a concentration of 150–250 µg/ml. For saturation experiments, 0.25 ml aliquots of tissue homogenate are incubated in duplicate with increasing concentrations of [$^3$H] Spiperone (70.3 Ci/mmol; 10–3000 pM final concentration) for 30–120 minutes at 22° C. in a total volume of 1 ml. For competition binding experiments, assays are initiated by the addition of 0.25 ml of membrane and incubated in duplicate with the indicated concentrations of competing ligands ($10^{-14}$–$10^{-3}$M) and [$^3$H]Spiperone (100–300 pM) in either the absence or presence of 200 uM GPP(NH)$^p$(5'/guanylylimidodiphosphate), where indicated, for 60–120 min at 22° C. Assays are terminated by rapid filtration through a Titertek cell harvester and the filters subsequently monitored for tritium as described by Sunahara, R. K. et al., Nature, 346, 76–80 (1990). For all experiments, specific [$^3$H]Spiperone binding is defined as that inhibited by 1–10 µM(+) Butaclamole or 1 µM Spiperone. Both saturation and competition binding data are analyzed by the non-linear least square curve-fitting program Ugand run on a digital Micro-PP-11 as described by Sunahara et al.

Approximately 80 compounds of the present invention were tested using the above procedure. All such compounds tested displaced [$^3$H]-spiperone binding with a $K_i$ of less than 1 µM.

The present invention is illustrated by the following examples. It will be understood, however, that the invention is not limited to the specific details of these examples. Melting points are uncorrected.

EXAMPLE 1

1-(4-Fluoro-phenyl)-4-oxiranylmethyl-piperazine

A mixture of 2.5 gm of 1-(4-fluoro-phenyl)-piperazine, 3.0 gm of 2S-(+)glycidyl 3-nitrobenzensulfonate (available from Aldrich) and 15 ml dimethylformamide (DMF) was kept for 12 hours at ambient temperature.. Thirty milliliters of water was added and the mixture was extracted with methylene chloride ($CH_2Cl_2$). The $CH_2Cl_2$ extract was collected, washed with 20 ml water and dried over sodium sulfate ($Na_2SO_4$). The crude product (3.5 gm of an oil) obtained after removing the solvents was purified by using chromatography: solid phase (SiO$_2$; 40 µm: Baker); eluent 5% methanol (CH$_3$OH) in chloroform (CHCl$_3$). A sample of this purified material showed a M+/z of 236 and had an optical rotation of $[\alpha]_D$=–15.54 (c=1.1, CHCl$_3$).

EXAMPLE 2

1-Oxiranylmethyl-1H-benzoimidazole

A mixture of 2.7 gm of 1-H-benzoimidazole, and 1 gm sodiumhydride (60%) in 30 ml DMF was kept for 0.3 hours at ambient temperature. Six grams of 2R—(–) glycidyl 3-nitrobenzenesulfonate (available from Aldrich) was added and the mixture was stirred for 2 hours. The mixture was added to 100 ml ice and water and extracted with ethyl acetate. The ethyl acetate extract was collected, washed with 20 ml water and dried over Na$_2$SO$_4$. The crude product (6.5 gm of an oil) obtained after removing the solvents was purified by using chromatography: solid phase (silicon dioxide (SiO$_2$); 40 µm; Baker); eluent 2% CH$_3$OH in CHCl$_3$. A sample of this purified material showed a M+/z of 175.

EXAMPLE 3

1-Benzoimidazol-1-yl-3-[4-(4-fluoro-phenyl)-piperazin-1yl]-propan-2-ol (both enantiomers)

A mixture of 0.26 gm of 1-H-benzoimidazole and 0.097 gm sodium hydride (60%) in 6 ml N,N-dimethylformamide (DMF) was kept for 0.3 hours at ambient temperature. 1-(4-fluoro-phenyl)—4—(–)oxiranylmethyl-piperazine (0.52 gm) was added and the mixture was stirred for 12 hours. This mixture was added to 10 ml ice and water and extracted with chloroform. The chloroform extract was collected, washed with 20 ml water and dried over Na$_2$SO$_4$. The crude product (1.0 gm of an oil) obtained after removing the solvents was purified using chromatography: solid phase (Sia$_2$; 40 µm; Baker); eluent 2% CH$_3$OH in CHCl$_3$. A sample of this purified material showed a M+/z of 355. It was transformed into its hydrochloride salt by treating an ethanolic suspension of this material with a mixture of ethyl ether/HCl. This salt had a melting point of 246°–247° C. and exhibited an optical rotation of $[\alpha]_D$=+7.3 (c=0.5, MeOH).

A mixture of 2.0 gm of 1-oxiranylmethyl-1H-benzoimidazole, 2.37 gm of 1-(4-fluorophenyl)piperazine and 25 ml ethanol was stirred at 80° C. for 48 hours. This mixture was added to 25 ml ice cold aqueous sodium hydroxide (NaOH) solution and extracted with CH$_2$Cl$_2$. The CH$_2$Cl$_2$ extract was collected, washed with 20 ml water and desiccated with Na$_2$SO$_4$. The crude product (94.18 gm of an oil) obtained after removal of solvents was purified using flash chromatography: solid phase (SiO$_2$; 40 µM; Baker); eluent 5% CH$_3$OH in CH$_2$Cl$_2$. A sample of this purified material (2.14 gm) was transformed into its hydrochloride salt by treating an ethanolic suspension of this material with a mixture of ethyl ether/HCl. This salt had a melting point of 238°–240° C. and exhibited an optical rotation of $[a]_D$= –7.3 (c=0.5, MeOH).

EXAMPLE 4

1-{3-[4-(4-Fluoro-phenyl)-piperazin-1-yl]-propyl}-1H-benzoimidazole

A mixture of 5.0 gm of {3-[4-(4-fluoro-phenyl)-piperazin-1-yl]-propyl}-(4-fluoro, 2-amino-phenyl)-amine, 18 ml of formic acid and 75 ml formamide was kept for 12 hours at 140–145° C. Water (300 ml) was added, and the mixture was made alkaline with ammonium hydroxide (NH$_4$OH) and extracted with ethyl acetate. The ethyl acetate extract was collected, washed with water (2×20 ml) and dried over Na$_2$SO$_4$. The crude product obtained after removal of solvents was purified using chromatography: solid phase (SiO$_2$; 40 µm; Baker); eluent 2% CH$_3$OH in CHCl$_3$. A sample of this purified material (2.2 gm) was transformed into its hydrochloride salt by treating an ethanolic suspension of this material with a mixture of ethyl ether/HCl. This salt exhibited a melting point of 236° C. and a mass of 356.18.

EXAMPLE 5

N-(2-Nitro4-fluorophenyl)-3-[4-(4-fluorophenyl) piperazin-1-yl]propionamide

A mixture of 14.8 gm of N-(2-nitro-4-fluorophenyl)-3-bromo-propionamide, 9.0 gm of 1 -(4-fluoro-phenyl)-piperazine, 6.46 gm of diisopropylethylamine and 150 ml DMF was kept for 48 hours at 150° C. Water (300 ml) was added at ambient temperature and the mixture was extracted with CHCl$_3$. The CHCl$_3$ extract was collected, washed with 20 ml water and dried over Na$_2$SO$_4$. The crude product obtained after removing the solvents was purified by using chromatography: solid phase (SIO$_2$; 40 µm; Baker); eluent CHCl$_3$. A sample of this purified material (12.7 gm) exhibited the following data. M+/z of 405.

EXAMPLE 6

{3-[4-(4-Fluorophenyl)-piperazin-1-yl]-propyl}-(2-aminophenyl)amine

A mixture of 1.03 gm of N-(2-amino-4,4-fluorophenyl)-3-[4-(4-fluorophenyl)-piperazin -1-yl)-propionamide and 8.5 ml of a solution of 1.0M lithium aluminum hydride in THF (added at a temperature of 9 ° C. over a period of 0.3 hours) and 10 ml THF was kept for 12 hours at 20°–25° C. Upon the slow addition of 1.7 ml 10% aqueous sodium hydroxide (NaOH), the mixture was treated with magnesium sulfate (MgSO$_4$) and the THF layer separated. The crude product, obtained after removing the solvent, was purified using standard chromatography: solid phase (SiO$_2$; 40pm; Baker); eluent 5% ethanol in ethyl acetate. A sample of this purified material (0.22 gm) exhibited the following data. M+/z of 361.

EXAMPLE 7

N-(2-Amino-4-fluorophenyl)-3-[4-(4-fluorophenyl)-piperazin-1-yl]propionamide

A mixture of 3.0 gm of N-(2-nitro4-fluorphenyl)-3-[4-(44luorophenyl)-piperazin-1-yl]-propionamide, 1 gm 5% palladium on carbon, 100 ml ethanol and 10 ml conc. hydrochloric acid was kept on a Parr Shaker in the presence of 45 psi hydrogen gas at 20–25° C. Upon cessation of hydrogen gas uptake, the mixture was purged with nitrogen and the ethanol layer separated. The crude product, obtained after removal of solvents, was purified by using standard chromatography: solid phase (SiO$_2$; 40 µm; Baker) eluent 5% ethanol in ethyl acetate. A sample of this purified material (0.22 gm) exhibited the following data. M+/z of 375.

EXAMPLE 8

N-(2-Nitro-4-fluorophenyl)-3-bromopropionamide

A mixture of 7.8 gm of 4-fluoro-2-nitroaniline, 8.57 gm of 3-bromo propionylchloride (added at a temperature of 0° C. over a period of 0.3 hours), 6.5 gm of diisopropylethylamine and 150 ml CH$_2$Cl$_2$ was kept for 48 hours at 20–25° C. Water (300 ml) was added and the mixture was extracted with CH$_2$C$_2$. The CH$_2$Cl$_2$ extract was collected, washed with water (2×20 ml) and desiccated wtih Na$_2$SO$_4$. The crude product (14.7 gm) obtained after removal of solvents was used without further purification. A sample of this crude material (14.79 gm) exhibited the following data. M+/z of 292.

EXAMPLE 9

4-[3-(2-Oxo-2,3-dihydro-benzoimidazol-1-yl)-propyl]-piperazine-1-carboxylic acid tert-butyl ester A mixture of 5.0 gm of 1 -t-butoxycarbonyl piperazine, 6.26 gm of 1-(3-chloro propyl)-2,3-dihydro-1H-benzimidazol-2-one (available from Janssen) and 4.16 gm diisopropylethylamine in 150 ml ethanol was kept for 12 hours at 80° C. Upon cooling to ambient temperature, 100 ml water was added and the mixture is extracted with CHCl$_3$. The CHCl$_3$. The CHCl$_3$ extract was collected, washed with 20 ml water and dried over Na$_2$SO$_4$. After removing solvents 10 gm of a yellowish oil was obtained which was used without further purification in Example 10.

EXAMPLE 10

1-[3(Piperazine-1-yl)propyl]-2,3-dihydro-1H-benzimidazol-2-one

A saturated solution of hydrochloric acid in 2 ml methanol and of 0.43 gm of 1-{4-[3-(t-butoxycarbonyl) piperazine-1-yl]propyl}-2,3-dihydro-1h-benzimidazol-2-one was kept for 1 hour at 50° C. Upon cooling to ambient temperature the solvent was removed, and the residue suspended in 10 ml water made basic with aqueous ammonium hydroxide solution. The aqueous layer was extracted with CHCl$_3$. The CHCl$_3$ extract is collected, washed with 20 ml water and dried over Na$_2$SO$_4$. After removing solvents, 0.207 gm of a yellowish oil was obtained which was used without further purification in Example 11.

EXAMPLE 11

1-{3-[4-(5-Trifluoromethyl-pyridin-2-yl)-piperazin-1-yl]]-propyl}-1,3-dihydro -benzoimidazol-2-one A mixture of 0.054 gm of 2-chloro 5-trifluoromethyl pyridine, 0.115 gm of 1-[4-(3-piperazine -1-yl)propyl]-2,3-dihydro-1H-benzimidazol-2-one and 0.194 gm of diisopropylethylamine in 1.0 ml 1-methyl-2-pyrolidinone was kept-for 3 hours at 150° C. Upon cooling to ambient temperature and addition of 10 ml water the mixture was acidified with concentrated hydrochloric acid and extracted 2×5 ml ethyl ether. The aqueous layer was then neutralized with aqueous ammonium hydroxide solution and extracted with ethyl acetate. The ethyl acetate extract was collected, washed with 20 ml water and dried over Na$_2$SO$_4$. The crude product (0.085 gm) obtained after removing the solvents was purified using chromatography: solid phase (SIO$_2$; 40 µM; Baker); eluent 2% CH$_3$OH in CHCl$_3$. A sample of this purified material (0.015 gm) was transferred into its hydrochloride salt (mp: 183° C.) by treating an ethanolic suspension of this material with a mixture of ethyl ether/HCl. This sample exhibited an M+/z of 406.

EXAMPLE 12

5-Fluoro-1-[3-[4-(4-fluoro-phenyl)-piperazin-1yl]-propyl}-2-methyl-1H -benzoimidazole A mixture of 5.0 gm of (3-[4-4-fluoro-phenyl)piperazin-1-yl]-propyl)-(4-fluoro, 2-amino -phenyl) amine in 20 ml aceticacidanhydride and 100 ml pyridine was refluxed for 12 hours. The solvent was removed, the residue made alkaline with sodium hydroxide (NaOH) and extracted with methylene chloride (CH$_2$Cl$_2$). The CH$_2$Cl$_2$ layer was collected, washed with water (2×20 ml) and dried over Na$_2$SO$_4$. The crude product, obtained after removal of solvents, was purified using chromatography: solid phase (SiO$_2$; 40 µm; Baker); eluent 0.5–2% CH$_3$OH in CHCl$_3$. A sample of this purified material was transformed into its hydrochloride salt by treating an ethanolic suspension of this material with a mixture of ethyl ether/HCl. This salt exhibited a melting point of 238–240 and a M+/z of 371.

EXAMPLE 13

5-Fluoro-1-{3-[4-(4-fluoro-phenyl)-piperazin-1-yl]-propyl}-2-trifluoromethyl-1H -benzoimidazole A. 3-(2-Amino4-fluoro-phenylamino)-propan-1-ol A mixture of 9.12 gm of 3-(2-nitro-4-fluoro-phenylamino)-propan-1-ol and 4.0 gm of 10% Pd on carbon is suspended in 300 ml methanol and shaken at ambient temperature under hydrogen (40 psi) for 12 hours. Thereafter, insoluble materials are removed by filtration and the reaction mixture is concentrated to a dark brown oil (5.25 gm of crude 3-(2-amino4-fluoro-phenylamino)-propan-1-ol).

B. 1-(3-hydroxy-propyl)-2-trifluoromethyl-5-fluoro-1H-benzimidazole

A mixture of 5.1 gm of 3-(2-amino4-fluoro-phenylamino)-propan-1-ol in 50.0 ml of trifluoroacetic acid anhydride (TFAA) is heated under reflux for 5 hours. Excess TFAA is removed and the residue dissolved in 500 ml ethyl acetate. The ethyl acetate layer is and washed 2× with 100 ml 2N NaOH. The water layer is extracted with 3×200 ml ethyl acetate. The ethyl acetate layers are combined and tried over Na$_2$SO$_4$. The residue, obtained after removal of solvents, is purified by flash column chromatography (solid phase: SiO$_2$; eluent: gradient starting with hexane followed by a mixture of ethyl acetate/hexane 1:1). Obtained is a solid material consisting of 1-(3-hydroxy-propyl)-2-trifluoromethyl-5-fluoro-1H-benzimidazole.

C. 1-(3-methanesulfonyloxy-propyl)-2-trifluoromethyl-5-fluoro-1H -benzimidazole

To a cold (−25° C.), stirred mixture of 1-(3-hydroxy-propyl)-2-trifluoromethyl-5-fluoro-1H-benzimidazole (2.09 gm), triethylamine (2.22 ml) and methylene chloride (12 ml) is dropwise added a solution of methanesulfonic acid anhydride (2.78 gm) in 14 ml CH$_2$Cl$_2$. After complete addition, the mixture is warmed to ambient temperature, extracted with water (2×20 ml), dried over Na$_2$SO$_4$ and concentrated to a thick brown oil {crude methanesulfonyl ester of above 1-(3-hydroxy-propyl)-2-trifluoromethyl-5-fluoro -1H-benzimidazole}.

D. 5-Fluoro-1-{3-[4-(4-fluoro-phenyl)-piperazin-1-yl]-propyl}-2-trifluoromethyl -1H-benzoimidazole A mixture of above crude methan esulfonyl ester of 1-(3-hydroxy-propyl)-2-trifluoromethyl -5-fluoro-1H-benzimidazole, triethylamine (2.2 ml) and 4-fluorophenylpiperazine (2.87 gm) is dissolved in 14 ml ethanol and heated under reflux for 12 hours. The residue, obtained after removed of solvents, is dissolved in ethyl acetate and washed with water (2×10 ml). The ethyl acetate layer is concentrated and the products isolated by flash chromatography (solid phase: SiO$_2$; eluent: gradient elution starting with hexane followed by a mixture of ethyl acetate/hexane 1:1). Obtained is a solid material consisting of 5-fluoro-1-{3-[4-(4-fluoro-phenyl)-piperazin-1-yl]-propyl}-2-trifluoromethyl-1H-benzimidazole (M+/Z 424).

EXAMPLE 14

5-Fluoro-1-{3-[4-(4-fluoro-phenyl)-3,6-dihydro-2H-pyridin-1-yl]-propyl}-2-trifluoromethyl-1H-benzoimidazole To a refluxing, stirred mixture of 11.5 gm of 3-(2-nitro-4-fluoro-phenylamino)-propan -1-ol, 200 ml acetic acid and 15.1 ml acetic acid anhydride is added small portions of zinc (Zn) dust until no discoloration of the reaction mixture is observed (approx. 4 hours). Solids are removed by filtration, washed with acetic acid and the combined acetic acid layer concentrated to a black oil. This oily residue is dissolved in ethyl acetate and washed with 2×50 ml water. The organic layer is collected, the solvent removed and the residue treated with a mixture of 1N NaOH (150 ml)/dioxane (approx. 150 ml) until the hydrolysis of the intermediary 1-(3-acetoxy-propyl)-2-methyl-5-fluoro-1H-benzimidazole is completed. Thereafter, the mixture is concentrated to a dark brown oil. This oily product can be purified by flash chromatography (solid phase: $SiO_2$; eluent: gradient starting with ethyl acetate followed by ethyl acetate/ethanol 8:2). Obtained are 4.67 gm of 1-(3-hydroxy-propyl)-2-methyl-5-fluoro-1H-benzimidazole(M+/Z 421).

EXAMPLE 15

1-(3-methanesulfonyloxy-propyl)-2-methyl-5-fluoro-1H-benzimidazole

To a stirred, cold mixture (−25° C.) of 1-(3-hydroxy-propyl)-2-methyl-5-fluoro-1H -benzimidazole (1.99 gm), triethylamine (1.47 ml) and methylenechloride (40 ml) is dropwise added a solution of methanesulfonylchloride (0.96 ml) in 15 ml $CH_2Cl_2$. After complete addition, the mixture is warmed to ambient temperature, extracted with water (2×20 ml), dried over $Na_2SO_4$ and concentrated to a thick brown oil consisting of crude 1-(3-methanesulfonyloxy-propyl)-2-methyl-5-fluoro-1H -benzimidazole.

EXAMPLE 16

5-Fluoro-1-3-4-(t-butoxycarbonyl)-piperazin-1-yl]-propyl}-2-methyl-1H -benzoimidazole To a stirred, cold mixture (−25° C.) of 1-(3-hydroxy-propyl)-2-methyl-5-fluoro-1H -benzimidazole (0.6 gm), triethylamine (0.44 ml) and methylenechloride (10 ml) is dropwise added a solution of methanesulfonylchloride (0.24 ml) in 1.5 ml $CH_2Cl_2$. After complete addition, the mixture is warmed to ambient temperature, extracted with water (2×20 ml), dried over $Na_2SO_4$) and concentrated to a thick brown oil consisting of crude 1-(3-methanesulfonyloxy-propyl)-2-methyl-5-fluoro-1 H-benzimidazole. A mixture of this methanesulfonylester and t-butylpiperazine carboxylate (0.7 gm) is dissolved in 5 ml ethanol and heated under reflux for 12 hours. Thereafter, the solvent is removed, the residue dissolved in ethyl acetate and washed with water (10 ml). The ethyl acetate layer is concentrated and the products isolated by flash chromatography (solid phase: $SiO_2$; eluent: gradient starting with hexane followed by a mixture of ethyl acetate/hexane 1:1). Obtained is a solid material consisting of 5-fluoro-1-{3-[4-(t-butoxycarbonyl) -piperazin-1-yl]-propyl}-2-methyl-1H-benzoimidazole.

EXAMPLE 17

1-{3-[4-(6-Chloro-pyridazin-3-yl)-piperazin-1-]propyl}-5-fluoro-2-methyl-1H -benzoimidazole A mixture of crude methanesulfonylester of 1-(3-hydroxy-propyl)-2-methyl-5-fluoro-1H-benzimidazole (prepared from 0.68 gm of 1-(3-hydroxy-propyl)-2-methyl-5-fluoro-1H-benzimidazole as described before), 0.68 ml triethylamine and 0.97 gm of 4-(6-chloro-pyridazin-3-yl) piperazine is dissolved in 1.4 ml ethanol and heated under reflux for 12 hours. The solvent is removed, the residue dissolved in ethyl acetate and washed with water (2×10 ml). The ethyl acetate layer is concentrated and products isolated by flash chromatography (solid phase: $SiO_2$; eluent: gradient starting with ethyl acetate followed by a mixture of ethyl acetate/methanol 8:1). Obtained is a solid material consisting of 1-{3-[4-(6-chloro-pyridazin-3-yl)-piperazin-1-yl]-propyl}-5-fluoro methyl-1H-benzoimidazole (M+/Z388).

EXAMPLE 18

3-[3-(5-Fluoro-2-methyl-benzoimidazol-1-yl)-propyl]-2,3,4,4a,5,6-hexahydro-1H -pyrazino2-alquinoline A. 2.3,4,4a,5,6-Hexahydro-1H-pyrazino[1 2-alquinoline Bromo acetyl bromide (1.46 ml) is slowly added to a stirred mixture of 1,2,3,4-tetrahydroquinoline -2-carboxylic acid methylester (3.2 gm), triethylamine (2.9 ml) and 120 ml tetrahydrofurane. After the reaction proceeds for 1 hour precipitates are removed by filtration and the filtrate concentrated to a dark oil. This oil is dissolved in 120 ml ethanol and upon addition of benzylamine (3.7 ml) heated under reflux for 18 hours. Thereafter, solvents are removed and the residue partitioned between ethyl acetate (200 ml) and water (200 ml). The ethyl acetate layer is washed with water (2×20 ml), brine (1×50 ml) and dried over magnesium sulfate ($MgSO_4$). The ethyl acetate layer is concentrated and products isolated by flash chromatography (solid phase: $SiO_2$; eluent: gradient 25% ethyl acetate in hexane followed by 50% ethyl acetate hexane. Obtained are 1.9 gm of an orange colored solid that consists of the diketopiperazine derivative of N-benzyl glycine and 1,2,3,4-tetrahydroquinoline-2-carboxylic acid. ($C_{19}H_{18}N_2O_2$—Found: C, 74.45%; H, 5.99%; N, 9.23%).

B. 3-[3-(5-Fluoro-2-methyl-benzoimidazol-1-yl)-propyl]-2,3,4,4a,5,6-hexahydro-1H-pyrazino[1,2a-alquinoline A solution of above diketopiperazine ($C_{19}H_{28}N_2O_2$) (1.0 gm) in 20 ml tetrahydrofurane is added slowly to a slurry of 0.225 mg of $LiAlH_4$ in 25 ml THF. After complete addition the mixture is refluxed under nitrogen for 12 hours. The mixture is brought to ambient temperature, quenched with aqueous $Na_2SO_4$ solution and filtered through Celite®. The filtrate is concentrated and products isolated by flash chromatography solid phase: $SiO_2$, eluent: 10% ethyl acetate in hexane. Obtained is a light orange oil (0.56 gm) consisting of 3-benzyl-2,3,4,4a,5,6-hexahydro-1H-pyrazino [1,2-a] quinoline (M+279). This product is shaken under 50 psi $H_2$ in presence of 200 mg palladium on carbon for 7 hours in 22 ml of 2% acetic acid/methanol at ambient temperature. Insoluble material is removed by filtration (Celite®), the filtrate concentrated and the residue partitioned between ethyl acetate and 1N NaOH. The ethyl acetate is washed with water and brine (each 2×10 ml), dried over $Na_2SO_4$ and concentrated. Obtained are 0.134 gm of 2,3,4,4a,5,6-hexahydro-1H-pyrazino[1,2-a]quinoline (M+/Z 189).

EXAMPLE 19

3-[3-(5-Fluoro-2-methyl-benzoimidazol-1-yl)-propyl]-2,3,4,4a,5,6-hexahydro-1H -pyrazino[1.2-alquinoline A mixture of crude methanesulfonylester of 1-(3-hydroxy-propyl)-2-methyl-5-fluoro-1H-benzimidazole (prepared from 0.72 mmol of 1-(3-hydroxy-propyl)-2-methyl-5-fluoro-1H-benzimidazole as described before), triethylamine (0.2 ml) and 2,3,4,4a,5,6-hexahydro-1H- pyrazino[1,2-a]quinoline (0.1 gm) is dissolved in 10 ml ethanol/tetrahydrofurane (1/1) and heated under reflux for 12 hours. Thereafter, solvents are removed, the residue dissolved in ethyl acetate and the ethyl acetate layer washed with water (2×10 ml). The ethyl acetate layer is concentrated and products isolated by high pressure liquid chromatography using as stationary phase a Waters C18 Bondapak 125Å column; eluent: 70% methanol/water, flow 10 ml/min). Obtained is 3-[3-(5-fluoro-2-methyl-benzoimidazol-1-yl)-propyl]-2,3,4,4a,5,6-hexahydro-1H-pyrazino [1,2-a] quinoline (62 mg). This product is transformed into its methanesulfonate salt by treating a solution of above material in methylenechloride with methane sulfonic acid. $C_{23}H_{27}FN_4 \times CH_3O_3S$—Found: C, 56.45; H, 6.91; N, 10.97.

EXAMPLE 20

1-(5-Fluoro-2-methyl-benzoimidazol-1-yl)-3-[4-(4-fluoro-phenyl)-piperazin-1-yl]-propan-2-ol A. 1-(4-Fluoro-2-nitro-phenylamino)-3-[4-(4-fluoro-phenyl)-piperazin-1-yl]-propan-2-ol A mixture of 2.84 gm of 1-(4-fluoro-phenyl)-4-oxiranylmethyl-piperazine; 2.6 ml of benzylamine and 25 ml ethanol is stirred at 80° C. for 6 hours. This mixture is added to 25 ml ice-cold aqueous NaOH solution and extracted with $CH_2Cl_2$. The $CH_2Cl_2$ extract is collected, washed with 20 ml water and desiccated with $Na_2SO_4$. The crude product (4.18 gm of an oil) obtained after removal of solvents can be purified using flash chromatography: Solid phase: ($SiO_2$: 40 μm; Baker); eluent: 5% $CH_3OH$ in $CH_2Cl_2$. This material (3.23 gm) is debenzylated by stirring a methanolic solution (100 ml) of above material in the presence of ammonium formate (3.9 gm) and palladium on carbon (3.2 gm) for 12 hours. The corresponding primary amine is isolated by removing insoluble materials by filtration (celite) and concentrating the filtrate. Obtained is an oil that solidifies upon standing. A sample of this crude intermediate product (1.17 gm) is dissolved in 50 ml toluene and heated in the presence of 2,4-difluoro -nitrobenzene (0.5 gm) and potassium carbonate (0.7 gm) for 18 hours). The residue, obtained after removal of solvents, is partitioned between ethyl acetate (30 ml) and water (10 ml). The ethyl acetate layer is washed with water and brine (each 2×5 ml) and dried over anhydrous magnesium sulfate. The ethyl acetate layer is concentrated and the residue purified by flash chromatography on $SiO_2$ eluent ethyl acetate providing the intermediate (1-(4-fluoro-2-nitro-phenylamino)-3-[4-(4-fluoro-phenyl)-piperazin-1-yl]-propan-2-ol.

B. 1-(5-Fluoro-2-methyl-benzoimidazol-1-yl)[4-(4-fluoro-phenyl)-2-i-piperazin-1-yl]-propan-2-ol To a heated solution of 1-(4-fluoro-2-nitro-phenylamino)-3-[4-(4-fluoro-phenyl) -piperazin-1-yl]-propan-2-ol (0.73 gm) in acetic acid (20 ml) conaining acetic acid anhydride (0.4 ml) are added small portion of zinc dust (1.26 gm) over a period of 3 hours. Thereafter, the mixture is brought to ambient temperature, insoluble materials are removed by filtration (Celite®) and the filtrate is concentrated. This concentrate is partioned between ethyl acetate (50 ml) and aqueous sodium bicarbonate solution (30 ml). The ethyl acetate layer is washed with water and brine (each 2×10 ml) and dried over magnesium sulfate. Products are isolated by flash column chromatography, stationary phase: $SIO_2$ (40 μm, Baker); eluent: hexane followed by 50% ethyl acetate in hexane. Obtained are two products: (1)1-(5-fluoro-2-methyl-benzoimidazol-1-yl)-3-[4-(4-4-fluoro-phenyl)-piperazin-1-yl]-propan-2-ol and (2) acetic acid 2-(5-fluoro-2-methyl -benzoimidazol-1-yl)-1-[4-(4-fluoro-phenyl)-piperazin-1-ylmethyl]-ethyl ester. M.p. 108–110° C.

EXAMPLE 21

5Fluoro-1-{3-[4-(fluoro-phenyl)-piperazin-1-yl]-2-methoxy-propyl}-2-methyl-1H -benzoimidazole A mixture of 1-(5-fluoro-2-methyl-benzoimidazol-1-yl)-3-[4-(4-fluoro-phenyl) -piperazin-1-yl]-propan-2-ol (0.063 gm) sodium hydride (0.015 gm) in 10 ml tetrahydrofuran is stirred for 20 minutes under nitrogen where upon methyliodide (0.18 ml) is added. After 12 hours, solvents are removed and the residue partitioned in ethyl acetate (20 ml) water (10 ml). The ethyl acetate layer is washed with brine (2×2 ml), tried over sodium sulfate. After removal of solvents products are isolated by flash column chromatography solid phase: $SiO_2$; eluent: gradient 2% ethanol in methylene chloride followed by 5% of ethanol in methylene chloride obtained is 5-fluoro-1-{3-[4-(4-fluoro-phenyl)-piperazin-1-yl]-2-methoxy-propyl}-2-methyl-1H-benzoimidazole as an oil. This compound can be transformed into its maleate salt by treating its ehteric solution with maleic acid and collecting the precipitate. M.p. 70–77° C.

EXAMPLE 22

5-Fluoro-1-{3-[4-(4-fluoro-phenyl)-piperazin-1-yl]-2-methyl-propyl-2-methyl-1H-benzoimidazole A. 3-(4-Fluoro-2-nitro-phenylamino)-2-methyl-propan-1-ol 3-Amino-2-methyl-propan-1-ol (5.1 gm) dissolved in 30 ml toluene is heated in the presence of 2,4-difluoro-nitrobenzene (3.25 gm) and potassium carbonate (2.1 gm) for 18 hours. The residue, obtained after removal of solvents, is partitioned between ethylacetate (300 ml) and water (100 ml). The ethyl acetate layer is washed with water and brine (each 2×50 ml) and dried over anhydrous magnesium sulfate. The ethyl acetate layer is concentrated and products isolated by flash chromatography, solid phase: $SiO_2$; eluent: gradient 10% ethyl acetate in hexane followed by 20% ethyl acetate in hexane, providing 3-(4-fluoro-2-nitro-phenylamino)-2-methyl-propan-1-ol (5.62 gm). $C_{10}H_{13}FN_2O_3$—Found: C, 52.46; H, 5.88; N, 12.41.

B. Methanesulfonic acid 3-(4-fluoro-2-nitro-phenylamino)-2-methylpropyl ester

To a cold (−25 ° C.), stirred mixture of 3-(4-fluoro-2-nitro-phenylamino)-2-methyl -propan-1-ol (2.0 gm), triethylamine (1.82 ml) in methylenechloride (50 ml) is dropwise added a solution of methanesulfonic acid anhydride (1.6 gm) in 50 ml $CH_2Cl_2$. After complete addition, the mixture is warmed to ambient temperature, extracted with water (2×20 ml), dried over $Na_2SO_4$ and concentrated to a thick brown oil crude methanesulfonic acid 3-(44luoro-2-nitro-phenylamino)-2-methyl-propyl ester (2.74 gm).

C. (4-Fluoro-2-nitro-phenyl)-{3-[4-(4-fluoro-phenyl)-piperazin-1-yl]-2-methyl -propyl-amine A mixture of above crude methanesulfonic acid 3-(4-fluoro-2-nitro-phenylamino) -2-methyl-propyl ester (2.6 gm), triethylamine (2.5 ml) and 4-fluorophenylpiperazine (3.7 gm) is dissolved in 100 ml ethanol and heated under reflux for 12 hours. The residue, obtained after removal of solvents, is dissolved in ethyl acetate 400 ml and washed with water (2×100 ml). The ethyl acetate layer is concentrated and the products are isolated by flash chromatography (solid phase: $SiO_2$; eluent 25% hexane in ethyl actate). Obtained is an orange colored solid consisting of (4-fluoro-2-nitro-phenyl)-{3-[4-(4-fluoro-phenyl)-piperazin-1-yl]-2-methyl-propyl}-amine. $C_{20}H_{24}F_2N_4O_2$—Found; C, 61.37; H, 6.21; N, 14.51.

D. 5-Fluoro-1-1-{3-[-4-(4-fluoro-phenyl)-piperazin-1-yl]-2-methyl-propyl-2-methyl-1H-benzoimidazole To a heated, refluxing and stirred mixture of 1.5 gm of (4-fluoro-2-nitro-phenyl) -{3-[4-(4-fluoro-phenyl)-piperazin-1-yl]-2-methyl-propyl}-amine, acetic acid (45 ml) and acetic acid anhydride (0.59 ml) are added small portions of Zn dust (2.7 gm) until no further discoloration of the reaction mixture is observed (approx. 4 hours). Thereafter, solids are removed by filtration, insolubles washed with acetic acid and the combined acetic acid layer concentrated to a black oil. This oil residue is dissolved in ethyl acetat (100 ml) and washed with 2×20 ml water. The ethyl acetate layer is dried over sodium sulfate and concentrated to a dark brown oil. Products are isolated by flash chromatography (solid phase: $SiO_2$; eluent: gradient starting with 25% ethyl acetate in hexane followed by 75% ethyl acetate in hexane). Obtained are 2.0 gm of a solid, 5-fluoro -1-{3-[4-(4-fluoro-phenyl)-piperazin-1-yl]-2-methyl-propyl}-2-methyl-1H-benzoimidazole. This solid can be transferred into its methanesulfonate salt by treating an ethanolic solution of the free base with methanesulfonic acid, concentrating this solution, trituating the residue with ethyl ether and collecting the solids. M.p. 84–91° C.

EXAMPLE 23

5-Fluoro-1-{3-[4-(4-fluoro-phenyl)-piperazin-1-yl]-butyl}-2-methyl-1H -benzoimidazole A. 2-[4-(4-Fluoro-phenyl)-piperazin-1-yl]-propan-1-ol A mixture of methanesulfonic acid 2-[[(4-fluoro-phenyl)-(2-methanesulfonyloxy -ethyl)-amino]-ethyl ester prepared in situ from 9.1 gm of methansulfonic acid anhydride, 6.92 gm of 2-[(4-fluoro-phenyl)-(2-hydroxy-ethyl)-amino]-ethanol and 12.1 ml triethylamine and 50 ml methylenechloride) and 5.22 gm of (R)(-)2-amino 1-propanol in 20 ml ethanol is heated under reflux for 5 hours. The residue, obtained after removal of solvents, is dissolved in ethyl acetate (100 ml) and washed with water (2×20 ml). The ethyl acetate layer is concentrated and the products isolated by flash chromatography (solid phase: $SiO_2$; eluent: ethyl acetate). Obtained is a solid material (3.3 gm) consisting of 2-[4-(4-fluoro-phenyl)-piperazin-1-yl]-propan-1-ol.

B. 3-[4-(4-Fluoro-phenyl)-piperazin-1-yl]-butyronitnile

To a mixture of 2-[4-(4-fluoro-phenyl)-piperazin-1-yl]-propan-1-ol (1.7 gm) and 4-methylmorpholine (1.18 ml) in 6 ml chloroform is added 1.86 gm of methansulfonic acid anhydride in 5 ml chloroform at -15° C. The reaction is brought to ambient temperature after 30 minutes and t-butylammonium cyanide (9.6 gm) is added. After 12 hours solvents are removed and the residue partitioned between ethyl acetate water. The ethyl acetate layer is washed with water (4×20 ml), brine (2×1 ml) and dried over sodium sulfate. The ethyl acetate layer is concentrated and the products isolated by flash chromatography (solid phase: $SiO_2$; eluent: 30% ethyl acetate in hexane). Obtained is an oily material (1.2 gm) consisting of 3-[4-(4-fluoro-phenyl)-piperazin-1-yl]-butyronitrile.

C. (4-Fluoro-2-nitro-phenyl)-{3-[4-(4-fluoro-phenyl)-piperazin-1-yl]-butyl}-amine 3-[4-(4-fluoro-phenyl)-piperazin-1-yl]-butylamine. A mixture of 3-[4-(4-fluoro -phenyl)-piperazin-1-yl]-butyronitrile (0.84 gm), 0.811 gm of cobalt chloride ($CoCl_2$, 0.811 gm) and sodium borohydride (1.29 gm, added slowly over a period of 2 hours) in 35 ml methanol is stirred for 12 hours. Insoluble materials are removed by filtration and the filtrate is concentrated and the residue partitioned between ethyl acetate and 1N sodium hydroxide. The ethyl acetate layer is washed with water (4×20 ml), brine (2×10 ml) and dried over sodium sulfate. The ethyl acetate layer is concentrated and the crude product consisting of 3-[4-(4-fluoro-phenyl)-piperazin-1-yl]-butylamine (0.65 gm) is used as is.

3-[4-(4-Fluoro-phenyl)-piperazin-1-yl]-butylamine (0.65 gm) dissolved in 30 ml toluene is heated in the presence of 2,4-difluoro-nitrobenzene (0.49 gm) and potassium carbonate (0.43 gm) for 18 hours. The residue, obtained after removal of solvents, is partitioned between ethyl acetate (100 ml) and water (50 ml). The ethyl acetate layer is washed with water and brine (each 2×25 ml) and dried over anhydrous magnesium sulfate. The ethyl acetate layer is concentrated and products isolated by flash chromatography, (solid phase: $SiO_2$; eluent: gradient 10% ethyl acetate in hexane followed by 20% ethyl acetate in hexane), providing (4-fluoro-2-nitro-phenyl)-{3-[4-(4-fluoro-phenyl)-piperazin-1-yl]-butyl}-amine as an orange red colored solid.

D. 5-Fluoro-1-{3-[4-(4-fluoro-phenyl)-piperazin-1-yl]-butyl}-2-methyl-1H -benzoimidazole To a refluxing, stirred mixture of (4-fluoro-2-nitro-phenyl)-{3-[4-(4-fluorophenyl) piperazin-1-yl]-butyl}-amine (0.38 gm), 10 ml acetic acid are added small portions of Zn dust (excess) until a nearly colorless reaction mixture is obtained approx. 4 hours). Insolubles are removed by filtration, washed with acetic acid and the combined acetic acid layer concentrated to a black oil. This oily residue is dissolved in ethyl acetate (50 ml) and washed with 2×10 ml water and brine. The organic layer is collected, the sovent removed and the residue purified by flash chromatography (solid phase: $SiO_2$; eluent: gradient starting with ethyl acetate followed by ethyl acetate/methanol 8:2). Obtained are 0.1 gm of 5-fluoro-1-{3-[4-(4-fluoro-phenyl)-piperazin-1-yl]-butyl}-2-1H-benzoimidazole. (M+/Z 384.47).

EXAMPLE 24

5-Fluoro-1-{3-[4-(4-fluorophenyl)-piperazin-1-yl]-butyl}-1,3-dihvdro-benzimidazol -2-one The title compound was prepared using the procedure depicted in scheme 5. M+/z 386. M.p. 188–193° C.

We claim:

1. A compound of Formula (I)

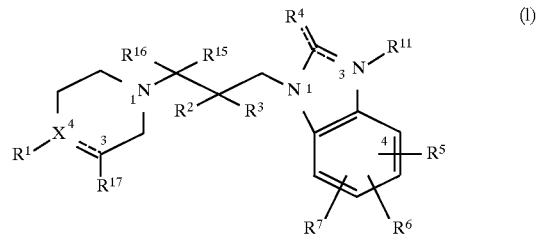

wherein each of the dotted lines represents an optional double bond;

X is or nitrogen;

$R^1$ is $(C_1-C_4)$alkyl; benzyl; aryl selected from phenyl, indanyl and naphthyl, or heteroaryl selected from pyridyl, thienyl, furyl, thiazolyl, isothiazolyl, oxazolyl, isoxazolyl, triazolyl, quinolyl and imidazolyl; wherein said $(C_1-C_4)$alkyl, phenyl moiety of said benzyl, aryl, and heteroaryl may be substituted with from zero to two substituents independently selected from chloro, fluoro, bromo and iodo; $(C_1-C_6)$alkyl optionally substituted with from one to three fluorine atoms $(C_1-C_6)$ alkoxy optionally substituted with from one to three fluorine atomsl cyano; nitro; hydroxyl; —C(=O)R$^8$; aryl; and heteroaryl wherein said aryl is selected from phenyl, indanyl and naphthyl and said heteroaryl; is selected from pyridyl, thienyl, furyl, thiazolyl, isothiazolyl, oxazolyl, isoxazolyl, triazolyl, quinolyl and imidazolyl; further wherein said aryl is optionally mono -substituted by chloro or fluoro;

one of R$^2$ and R$^3$ is hydroxy and the other is hydrogen or (C$_1$–C$_6$)alkyl;

R$^4$ is hydrogen, sulfur, oxygen, (C$_1$–C$_6$)alkyl, amino, —NHR$^{10}$, —SR$^{10}$, OR$^{10}$ or CF$_3$;

R$^5$, R$^6$ and R$^7$ are independently selected from hydrogen; chloro, fluoro, bromo or iodo; cyano; (C$_1$–C$_6$)alkyl optionally substituted with from one to three fluorine atoms; (C$_1$–C$_6$)alkoxy optionally substituted with from one to three fluorine atoms; (C$_1$–C$_6$)alkylsulfonyl; (C$_1$–C$_6$)acylamino; (phenyl)(C$_1$–C$_6$)acylamino; (C$_1$–C$_6$)alkylamino; di-(C$_1$–C$_6$)alkylamino; aryl; and heteroaryl; wherein said aryl is selected from phenyl, naphthyl and indanyl, and said heteroaryl is selected from pyridyl, thienyl, furyl, thiazolyl, isothiazolyl, oxazolyl, isoxazolyl, triazolyl, quinolyl and imidazolyl;

R$^8$, R$^9$ and R$^{10}$ are independently selected from hydrogen and (C$_1$–C$_6$)alkyl; R$^{11}$ is hydrogen; (C$_1$–C$_6$)alkyl or benzyl; wherein phenyl moiety of said benzyl may optionally be substituted with from zero to two substituents independently selected from fluoro, chloro, bromo, or iodo; (C$_1$–C$_6$)alkyl optionally substituted with from one to three fluorine atoms; (C$_1$–C$_6$)alkoxy optionally substituted with from one to three fluorine atoms; amino; cyano; (C$_1$–C$_6$)alkylamino; and di-(C$_1$–C$_6$)alkylamino;

each of R$^{15}$ and R$^{16}$ is independently selected from hydrogen, methyl, cyano, —(C=O)—NH$_2$ and —CH$_2$—O—(C$_1$–C$_6$)alkyl; and R$^{17}$ is hydrogen or, when X is nitrogen, R$^7$ may optionally form, together with the carbon to which it is attached, R$^1$ and X, a tetrahydroquinoline ring;

or a pharmaceutically acceptable salt thereof;

with the proviso that: (a) when the five-membered ring of Formula (I) contains a double bond, R$^{11}$ is absent; (b) when R$^4$ is sulfur or oxygen, R$^4$ is double bonded to the ring carbon atom to which it is attached and said carbon atom is single bonded to both adjacent ring nitrogen atoms or when R$^4$ is hydroxyl, said ring carbon atom is double bonded to one said adjacent ring nitrogen atom as shown by said dotted line in Formula (I); and (c) when X is nitrogen and is double bonded to an adjacent ring carbon atom, R$^1$ is absent.

2. A compound according to claim 1 wherein X is nitrogen.

3. A compound according to claim 2, wherein R$^1$ is absent.

4. A compound according to claim 1, wherein said compound is selected from the group consisting of:

5-Fluoro-1-{3-[4-(4-fluoro-phenyl)-piperazin-1-yl]butyl}-1,3-dihydro-benzoimidzol -2-one;

1-Benzoimidazol-1-yl-3-[4-(4-fluoro-phenyl)-piperazin-1-yl]-propan-2-ol;

1-(5-Chloro-benzoimidazol-1-yl)-3-[4-(4-fluoro-phenyl)-piperazin-1-yl]-propan-2-ol;

1-{3-[4-(4-Fluoro-phenyl)-piperazin-1-yl]-propyl}-5-trifluoromethyl-1H -benzoimidazole;

1-{3-[4-(4-Fluoro-phenyl)-piperazin-1-yl]-propyl}-1H-benzoimidazole;

1-{3-[4-(4-Fluoro-phenyl)-piperazin-1-yl]-propyl}-3-methyl-1,3-dihydro -benzoimidazol-2-one;

1-Benzoimidazol-1-yl-3-(4-p-tolyl-piperazine-1-yl)-propan-2-ol;

1-Benzoimidazol-1-yl-3-(4-m-tolyl-piperazine-1-yl)-propan-2-ol;

1-Benzoimidazol-1-yl-3-(4-p-tolyl-piperazin-1-yl)-propan-2-ol;

1-Benzoimidazol-1-yl-{4chloro-phenyl)-phenyl-methyl]-piperazin-1-yl}-propan-2-ol;

1-Benzoimidazol-1-yl-3-4-(2-chloro-phenyl)-piperazin-1-yl]-propan-2-ol;

1-Benzoimidazol-1-yl-3-[4-(4-chloro-phenyl)-piperazin-1 -yl]-propan-2-ol;

1-Benzoimidazol-1-yl-3-[4-(3-chloro-phenyl)-piperazin-1 -yl]-propan-2-ol;

1-Benzoimidazol-1-yl-3-[4-(3-chloro-phenyl)-piperazin-1 -yl]-propan-2-ol;

1-Benzoimidazol-1-yl-3-(4-pyrimidin-2-yl-piperazin-1-yl)-propan-2-ol;

1-Benzoimidazol-1-yl-3-(4-naphthalen-1-yl-piperazin-1-yl)-propan-2-ol;

1-Benzoimidazol-1-yl-3-[4-(3-trifluoromethyl-phenyl)-piperazin-1-yl]-propan-2-ol;

1-Benzoimidazol-1-yl-3-(4-benzyl-piperazin-1-yl)-propan-2-ol;

1-Benzoimidazol-1-yl-3-4-(2-trifluoromethyl-benzyl)-piperazin-1-yl]-propan-2-ol;

1-Benzoimidazol-1-yl-3-[4-(2-ethoxy-benzyl)-piperazin-1-yl]- propan-2-ol;

1-Benzoimidazol-1-yl-3-{4-{3-(3-trifluoromethyl-phenyl)-propyl]-piperazin-1-yl}-propan-2-ol; and 1-Benzoimidazol-1-yl-3-{4-[2-(3-trifluoromethyl-phenyl)-ethyl]-piperazin-1-yl}-propan-2-ol.

5. A pharmaceutical composition for treating or preventing a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, ocular disorders, congestive heartfailure, chemical dependencies, vascularand cardiovasculardisorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising a dopaminergic effective amount of a compound according to claim 1 and a pharmaceutically acceptable carrier.

6. A method of treating or preventing a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, ocular disorders, congestive heart failure, chemical dependencies, vascular and cardiovascular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising an administering to said mammal a dopaminergic effective amount of a compound according to claim 1.

7. A pharmaceutical composition for treating or preventing a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, ocular disorders, congestive heart failure, chemical dependencies, vascular and cardiovascular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising a D4 receptor binding effective amount of a compound according to claim 1 and a pharmaceutically acceptable carrier.

8. A method of treating or preventing a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, ocular disorders, congestive heart failure, chemical dependencies, vascular and cardiovascular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising an administering to said mammal a D4 receptor binding effective amount of a compound according to claim 1.

9. A pharmaceutical composition for treating or preventing a disease or condition, the treatment or prevention of which can be effected or facilitated by altering dopamine mediated neurotransmission in a mammal, comprising a D4 receptor binding effective amount of a compound according to claim 1 and a pharmaceutically acceptable carrier.

10. A method of treating or preventing a disease or condition, the treatment or prevention of which can be effected or facilitated by altering dopamine mediated neurotransmission in a mammal, comprising administering to said mammal a D4 receptor binding effective amount of a compound according to claim 1.

* * * * *